United States Patent
Mukhopadhyay et al.

(10) Patent No.: US 9,493,763 B2
(45) Date of Patent: Nov. 15, 2016

(54) STABILIZED LACCASE ENZYME AND METHODS OF MAKING AND USING THE SAME

(71) Applicant: University of Calcutta, Kolkata, West Bengal (IN)

(72) Inventors: Arka Mukhopadhyay, Howrah (IN); Krishanu Chakraborti, Kolkata (IN); Anjan Kr. Dasgupta, Kolkata (IN)

(73) Assignee: UNIVERSITY OF CALCUTTA, Kolkata (IN)

( * ) Notice: Subject to any disclaimer, the term of this patent is extended or adjusted under 35 U.S.C. 154(b) by 0 days.

(21) Appl. No.: 14/413,635

(22) PCT Filed: Jul. 1, 2013

(86) PCT No.: PCT/IB2013/055396
§ 371 (c)(1),
(2) Date: Jan. 8, 2015

(87) PCT Pub. No.: WO2014/009849
PCT Pub. Date: Jan. 16, 2014

(65) Prior Publication Data
US 2015/0175999 A1 Jun. 25, 2015

(30) Foreign Application Priority Data

Jul. 9, 2012 (IN) .............................. 754/KOL/2012

(51) Int. Cl.
| | |
|---|---|
| *C12N 9/96* | (2006.01) |
| *C12N 11/14* | (2006.01) |
| *C12N 9/02* | (2006.01) |
| *D06L 3/11* | (2006.01) |

(52) U.S. Cl.
CPC .............. *C12N 9/96* (2013.01); *C12N 9/0061* (2013.01); *C12N 11/14* (2013.01); *D06L 3/11* (2013.01)

(58) Field of Classification Search
CPC .................................................. C12N 11/14
See application file for complete search history.

(56) References Cited

U.S. PATENT DOCUMENTS

| | | | |
|---|---|---|---|
| 5,795,855 | A | 8/1998 | Schneider et al. |
| 8,097,441 | B2 | 1/2012 | Peng et al. |
| 2001/0037532 | A1 | 11/2001 | Barfoed et al. |
| 2005/0089980 | A1 | 4/2005 | Kruus et al. |
| 2006/0147512 | A1 | 7/2006 | Sabin |

FOREIGN PATENT DOCUMENTS

| | | |
|---|---|---|
| GB | 2304107 A | 3/1997 |
| MX | PA05002751 A | 6/2005 |
| WO | WO-2004/023879 A1 | 3/2004 |
| WO | WO-2006/056838 A1 | 6/2006 |

OTHER PUBLICATIONS

Kandelbauer et al. Biotechnology and Bioengineering, 2004, 87(4):552-563.*
Pradhan et al. "Copper oxide nanoparticles induce oxidative stress, DNA strand breaks and laccase activity in aquatic fungi", 2011, meeting abstract, 1 page.*
Gajjar et al. J of Biological Engineer, 2009, 3(9):1-13.*
Baek et al. Science of the Total Environment, 2011, 409:1603-1608.*
Shraddha et al. Enzyme Research, 2011, p. 1-11.*
Barner, B. A., "Catechol," Published Online Sep. 15, 2008, Encyclopedia of Reagents for Organic Synthesis, 3rd Ed., L. Paquette, J. Wiley & Sons, New York, pp. 2116-2119. (2009).
Fiege, H., et al., "Phenol Derivatives," in Ullmann's Encyclopedia of Industrial Chemistry, Wiley-VCH, 62 pages. (Jun. 15, 2000).
Goor, G., "Hydrogen Peroxide," in Ullmann's Encyclopedia of Industrial Chemistry, Wiley-VCH, pp. 394-427. (Apr. 15, 2007).
Abadulla, E., et al., "Decolorization and detoxification of textile dyes with a laccase from Trametes hirsute," Applied and Environmental Microbiology, vol. 66, No. 8, pp. 3357-3362 (Aug. 2000).
Akhtar, M., et al., "Fungal delignification and biomechanical pulping of wood," In Advances in biochemical engineering and biotechnology, Berlin: Springer-Verlag, vol. 57, pp. 159-195 (1997).
Banat, I. M., "Microbial Decolorization of Textile-Dye-Containing Effluents: A Review," Bioresource Technology, vol. 58, pp. 217-227 (1996).
Behrendt, C.J., "Biomechanical pulping with Phlebiopsis gigantea reduced energy consumption and increased paper strength," Tappi journal, vol. 83, No. 9, pp. 65 (Sep. 2000).
Blánquez, P., et al., "Mechanism of textile metal dye biotransformation by Trametes versicolor," Water Research, vol. 38, No. 8, pp. 2166-2172 (Apr. 2004).
Bollag, J.M., et al., "Laccase-mediated detoxification of phenolic compounds," Appl. Environ. Microbiol., vol. 54, No. 12, pp. 3086-3091 (Dec. 1998).
Chawla, S., et al., "Fabrication of polyphenol biosensor based on laccase immobilized on copper nanoparticles/chitosan/multiwalled carbon nanotubes/polyaniline-modified gold electrode," Journal of Biotechnol., vol. 156, No. 1, pp. 39-45 (Oct. 20, 2011).
Cho, N.S., et al., "Removal of chlorophenols by fungal laccase in the presence of aromatic alcohols," Journal of the Faculty of Agriculture Kyushu University, vol. 52, No. 1, pp. 23-27 (2000).
Couto, S. R., and Herrera, J. L. T., "Industrial and biotechnological applications of laccases: A review," Biotechnology Advances, vol. 24, No. 5, pp. 500-513 (Sep.-Oct. 2006).
Couto, S. R., and Herrera, J. L. T., "Laccases in the textile industry," Biotechnology and Molecular Biology Review, vol. 1, No. 4, pp. 115-120 (Dec. 2006).
Couto, S. R., et al., "Production of Laccase by Trametes Hirsuta Grown in an Immersion Bioreactor and Its Application in the Decolorization of Dyes from a Leather Factory," Engineering in Life Sciences, vol. 4, Issue 3, pp. 233-238 (Jun. 2004).

(Continued)

*Primary Examiner* — Bin Shen
(74) *Attorney, Agent, or Firm* — Foley & Lardner LLP

(57) ABSTRACT

Provided herein are compositions and methods for enhancing enzyme activity, half-life, thermostability, enhanced activity at elevated temperature, and/or decreasing the pH dependency of laccase enzyme. Also provided are methods for using the composition comprising the stabilized enzymes.

24 Claims, 13 Drawing Sheets

(56) References Cited

OTHER PUBLICATIONS

Gianfreda, L. et al., "Laccases: a useful group of oxidoreductive enzymes," vol. 3, No. 1, pp. 1-26 (1999).

Hedin, P. A., et al., "Evaluation of flavonoids in *Gossypium arboreum* (L.) cottons as potential source of resistance to tobacco budworm," J. Chem. Ecol., vol. 18, No. 2, pp. 105-114 (1992).

Howard, R.S., et al., "Lignocellulose biotechnology: issues of bioconversion and enzyme production," African Journal of Biotechnology, vol. 2, No. 12, pp. 602-619 (Dec. 2003).

International Search Report and Written Opinion for International Patent Application No. PCT/IB2013/055396, mailed Jan. 10, 2014.

Leatham, G. F., et al., "Biomechanical pulping of aspen chips: energy savings resulting from different fungal treatments," Tappi Journal, vol. 73, No. 5, pp. 197-200 (May 1990).

Liao, C.-H., et al., "Biochemical characterization of pectate lyases produced by fluorescent Pseudomonads associated with spoilage of fresh fruits and vegetables," Journal of Applied Microbiology, vol. 83, Issue 1, pp. 10-16 (Nov. 25, 2003).

Mukhopadhyay, A., et al., "Improvement of thermostability and activity of pectate lyase in the presence of hydroxyapatite nanoparticles," Bioresource Technology, vol. 116, pp. 348-354 (2012).

Mukhopadhyay, A., et al., "Thermostability, pH stability and dye degrading activity of a bacterial laccase are enhanced in the presence of $Cu_2O$ nanoparticles," Bioresource Technology, vol. 127, pp. 25-36 (2013).

Ortega, N., et al., "Kinetic behaviour and thermal inactivation of pectinlyase used in food processing," International Journal of Food Science & Technology, vol. 39, No. 6, pp. 631-639 (Jun. 2004).

Pearce, C. I., et al., "The removal of colour from textile wastewater using whole bacterial cells: a review," Dyes Pigments, vol. 58, Issue 3, pp. 179-196 (Sep. 2003).

Pierce, J., "Colour in textile effluents—the origins of the problem," Journal of the Society of Dyers and Colourists, vol. 110, Issue 4, pp. 131-134 (Apr. 1994).

Pereira, L., et al., Gübitz GM (2005). "Environmentally friendly bleaching of cotton using laccases," Environ. Chem. Lett., vol. 3, pp. 66-69 (2005).

Raghukumar, C., et al., "Treatment of colored effluents with lignin-degrading enzymes: An emerging role of marine-derived fungi," Critical Reviews in Microbiology, vol. 34, No. 3-4, pp. 189-206 (2008).

Scott, G.M., et al., "Recent developments in biopulping technology at Madison, WI," Progress in Biotechnology, vol. 21, pp. 61-71 (2002).

Selvam, K., et al., "Pretreatment of wood chips and pulps with Fomes lividus and Trametes versicolor to reduce chemical consumption in paper industries," Asian Jr. of Microbiol. Biotechnol. Environ. Sci., vol. 8, No. 4, pp. 771-776 (2006).

Solbak, A. I., et al., "Discovery of Pectin-Degrading Enzymes and Directed Evolution of a Novel Pectate Lyase for Processing Cotton Fabric," Journal of Biological Chemistry, vol. 280, No. 10, pp. 9431-9438 (Mar. 11, 2005).

Taherzadeh, M.J., and Karimi, K., "Pretreatment of Lignocellulosic Wastes to Improve Ethanol and Biogas Production: A Review," Int. J. Mol. Sci., vol. 9, No. 9, pp. 1621-1651 (Sep. 2008).

Tzanov, T., et al., "Bio-preparation of cotton fabrics," Enzyme and Microbial Technology, vol. 29, Issues 6-7, pp. 357-362 (Oct. 4, 2001).

Van Beek, T.A., et al., "Fungal bio-treatment of spruce wood with Trametes versicolor for pitch control: Influence on extractive contents, pulping process parameters, paper quality and effluent toxicity," Biosour Technology, vol. 98, pp. 302-311 (2007).

Beg, Q. K. et al., "Microbial xylanases and their industrial applications: a review," Appl Microbiol Biotechnol, vol. 56, No. 3-4, pp. 326-338 (2001).

Bhandari, N., "Kinetic studies of corn stover saccharification using sulphuric acid," Biotech. Bioeng, vol. 26, pp. 320-327 (1984).

Brondani, D. et al., "PEI-coated gold nanoparticles decorated with laccase: A new platform for direct electrochemistry of enzymes and biosensing applications," Biosensors and Bioelectronics 42: 242-247 (2013).

Carrion, J., "Hemicellulose removal from corn stalk thermochemical treatment in aqueous medium," Lisbon, Portugal, 2.45-2.49 (1989).

Cavicchioli, R. et al., "Low-temperature extremophiles and their applications," Current Opinion in Biotechnology, vol. 13, pp. 253-261 (2002).

Collins, T. et al., "Use of glycoside family 8 xylanases in baking," J Cereal Sci, vol. 43, pp. 79-84 (2006).

Collins, T., et al., "Activity, stability and flexibility in glycosidases adapted to extreme thermal environments," J. Mol. Biol. vol. 328, pp. 419-428 (2003).

Couto, S. R. and Toca-Herrera, J. L., "Lacasses in the textile industry," Biotechnology and Molecular Biology Review, vol. 1, No. 4, pp. 115-120 (2006).

Couto, S. R. et al., "Industrial and biotechnological applications of laccases," A review; Biotechnology Advances, vol. 24, pp. 500-513 (2006).

Curreli, N., "Mild alkaline/ oxidative pretreatment of wheat straw," Process Biochemistry, vol. 32, pp. 665-670 (1997).

D'Amico, S. et al., "Activity—stability relationships in extremophilic enzymes," J. Biol. Chem., vol. 278, No. 10, pp. 7891-7896 (2003).

Feller, G. and Gerday C., "Psychrophilic Enzymes: Hot Topics in Cold Adaptation," Nature Review, Microbiology, vol. 1, pp. 200-208 (2003).

Garrote, G. et al., "Autohydrolysis of corncob:study of non-isothermal operation for xylooligosaccharide production," Journal of Food Engineering, vol. 52, No. 3, pp. 211-218 (2002).

Gaspar, M. et al., "Fractionation and utilization of corn fibre carbohydrates," Process Biochemistry, vol. 40, No. 3-4, 1183-1188 (2005).

Georlette, D. et al., "Structural and functional adaptations to extreme temperatures in psychrophilic, mesophilic and thermophilic DNA ligases," J. Biol. Chem., vol. 278, pp. 37015-37023 (2003).

Gerday, C. et al., "Cold—adapted enzymes: from fundamentals to biotechnology," Trends Biotechnol., vol. 18, pp. 103-107 (2000).

Ho, N.W.Y., et al., "Genetically engineered Saccharomyces yeast capable of effective cofermentation of glucose and xylose," Applied and Environmental Microbiology, vol. 64, pp. 1852-1859 (1998).

Huston, A. L., "Biotechnological Aspects of Cold-Adapted Enzymes," Psychrophiles: from Biodiversity to Biotechnology, pp. 347-363 (2008).

Kashyap, D. R. et al., "Applications of pectinases in the commercial sector: a review," Bioresource Technology, vol. 77, pp. 215-227 (2001).

Kuhad, R. C. et al., "Microbial Cellulases and Their Industrial Applications," Enzyme Research, vol. 2011, Article ID 280696, 11 pages (2011).

Lamptey, J., "Enhanced enzymatic hydrolysis of lignocellulosic biomass pretreatment by low-pressure steam autohydrolysis," Biotech. Lett., vol. 7, No. 7, pp. 531-534 (1985).

Lee, Y.Y. et al., "Kinetic and Modeling Investigation on Dilute-Acid Pretreatment of Hardwood, Hardwood Bark, and Corn Cobs/Stover Mixture Feedstocks," Annual Report for NREL Subcontract XAW-3-13441-01, pp. 114 (1995).

Lloyd, T., and Wyman, C.E., "Application of a depolymerization model for predicting thermochemical hydrolysis of hemicellulose," Applied Biochemistry and Biotechnology, vol. 105, pp. 53-67 (2003).

Lynd, L.R. et al., "Likely features and costs of mature biomass ethanol technology," Appl. Biochem. Biotechnol., vol. 57/58, pp. 741-761 (1996).

Margesin, R. and Schinner, F., "Biodegradation of organic pollutants at low temperatures," In Biotechnological Applications of Cold Adapted Organisms, pp. 271-289 (1999).

Moniruzzaman, M., et al., "Fermentation of corn fibre sugars by an engineered xylose utilizing Saccharomyces yeast strain," World Journal of Microbiology and Biotechnology, vol. 13, pp. 341-346 (1997).

(56) References Cited

OTHER PUBLICATIONS

Morita, R., "Psychrophilic bacteria," Bacteriol Rev, vol. 39, No. 2, pp. 144-169 (1975).

Narinx, E. et al., "Subtilisin from psychrophilic antarctic bacteria: characterization and site-directed mutagenesis of residues possibly involved in the adaptation to cold," Protein Eng., vol. 10, No. 11, pp. 1271-1279 (1997).

Ohgiya, S., "Biotechnology of enzymes from cold-adapted microorganisms," In: Margesin, R. and Schinner F. (Eds.) Spriger, 17-34 (1999).

O'Neill, C. et al., "Colour in textile effluents—sources, measurement, discharge consents and simulation: a review," J Chem Technol Biotechnol, vol. 74, pp. 1009-1018 (1999).

Russell, N. J., "Molecular adaptations in psychrophilic bacteria: Potential for biotechnological applications," Adv. Biochem. Eng. Biotechnol, vol. 61, pp. 1-21 (1998).

Sabri, A. et al., "Influence of moderate temperatures on myristoyl-CoA metabolism and acyl-CoA thioesterase activity in the psychrophilic antarctic yeast Rhodotorula aurantiaca," J. Biol. Chem., vol. 276, No. 16, pp. 12691-12696 (2001).

Sadasivam, S. and Manikam, A., "Biochemical Methods for agricultural sciences," New Age International publishing house, pp. 41-42 (1991).

Schultz, T.P. et al., "Steam explosion of mixed hardwood chips, rice hulls, corn stalk, and sugar cane bagasse," J. Agric. Food Chem., vol. 32, No. 5, pp. 1166-1172, (1984).

Sproessler, B.G., "Milling and baking," In Enzymes in Food Processing (Nagodawithana, T. and Reed, G., eds), pp. 293-320, (1993).

Sun, Y., and Cheng, J.Y., "Hydrolysis of lignocellulosic materials for ethanol production: a review," Bioresource Technology, vol. 83, pp. 1-11 (2002).

Timmis, K.N. and Pieper, D.H., "Bacteria designed for bioremediation," Trends Biotechnol., vol. 17, No. 5, pp. 201-204 (1999).

Tolan, J. S., and Foody, B., "Cellulase from submerged fermentation," Advanced Biochemical Engineering and Biotechnology, vol. 65, pp. 41-67 (1999).

Torget, R., et al., "Dilute-acid pretreatment of corn residues and short rotation woody crops," Appl. Biochem. Biotechnol., vol. 28/29, pp. 75-86 (1991).

Tucker, M.P. et al., "Effects of temperature and moisture on dilute-acid steam explosion pretreatment of corn stover and cellulase enzyme digestibility," Appl. Biochem. Biotechnol., vol. 105, No. (1-3), pp. 165-178 (2003).

Wyman, C.E., "Potential synergies and challenges in refining cellulosic biomass to fuels, chemicals, and power," Biotechnol Prog, vol. 19, pp. 254-262 (2003).

\* cited by examiner

STABILIZED LACCASE ENZYME AND METHODS OF MAKING AND USING THE SAME

CROSS-REFERENCE TO RELATED APPLICATIONS

This application is the U.S. National Stage filing under 35 U.S.C. §371 of PCT/IB2013/055396 with international filing date of Jul. 1, 2013, which claims the benefit of Indian Patent Application No. 754/KOL/2012, filed on Jul. 9, 2012, the entire contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Jun. 18, 2012, is named 91619707.txt and is 38,549 bytes in size.

BACKGROUND

Laccase (benzenediol: oxygen oxidoreductase; EC 1.10.3.2), is one of the extracellular glycoprotein enzymes expressed by microorganisms that degrade lignocellulosic material. The laccase molecule is a dimeric or tetrameric glycoprotein, which usually contains four copper atoms per monomer distributed in three redox sites. This enzyme catalyzes the oxidation of ortho and paradiphenols, aminophenols, polyphenols, polyamines, lignins and aryl diamines, as well as some inorganic ions coupled to the reduction of molecular dioxygen to water. Typically, laccase acts on phenolic substrates by catalyzing the oxidation of their phenolic hydroxyl groups to phenoxy radicals while dioxygen ($O_2$) is reduced to water.

SUMMARY

The foregoing summary is illustrative only and is not intended to be in any way limiting. In addition to the illustrative aspects, embodiments, and features described above, further aspects, embodiments, and features will become apparent by reference to the following detailed description.

Provided herein are compositions and methods related to laccase enzymes having enhanced activity, half-life, and/or thermal stability, and/or decreased pH dependency.

In some aspects, a composition is provided. In some embodiments, the composition includes at least one nanoparticle comprising cuprous oxide and at least one laccase enzyme in contact with the nanoparticle comprising cuprous oxide in which the enzyme is not immobilized on the nanoparticle.

In some embodiments, the composition includes at least one nanoparticle comprising magnesium chloride, manganese chloride, or calcium chloride and at least one laccase enzyme in contact with the nanoparticle comprising magnesium chloride, manganese chloride, or calcium chloride in which the enzyme is not immobilized on the nanoparticle.

In some aspects, methods of making a stabilized enzyme composition are provided. In some embodiments, the methods include: combining to form a mixture: a) a plurality of nanoparticles comprising cuprous oxide; and b) a laccase enzyme; under conditions in which the enzyme is in contact with the nanoparticle comprising cuprous oxide in which the enzyme is not immobilized on the nanoparticle.

In some embodiments, the methods include: combining to form a mixture: a) a plurality of nanoparticles comprising magnesium chloride, manganese chloride, or calcium chloride; and b) a laccase enzyme; under conditions in which the enzyme is in contact with the nanoparticle comprising magnesium chloride, manganese chloride, or calcium chloride in which the enzyme is not immobilized on the nanoparticle.

In some aspects, provided herein are methods of treating a substrate. In some embodiments, the method includes contacting the substrate with a composition including: i) at least one nanoparticle, comprising cuprous oxide; and ii) a laccase enzyme in contact with the nanoparticle comprising cuprous oxide in which the enzyme is not immobilized on the nanoparticle.

In some embodiments, the method includes contacting the substrate with a composition including: i) at least one nanoparticle, comprising magnesium chloride, manganese chloride, or calcium chloride; and ii) a laccase enzyme in contact with the nanoparticle comprising magnesium chloride, manganese chloride, or calcium chloride in which the enzyme is not immobilized on the nanoparticle.

In some aspects, kits are provided. In some embodiments, the kit includes i) at least one nanoparticles comprising cuprous oxide, ii) a laccase enzyme, in which the enzyme is not immobilized on the nanoparticle. In some embodiments, the kit includes i) at least one nanoparticles comprising magnesium chloride, manganese chloride, or calcium chloride, ii) a laccase enzyme, in which the enzyme is not immobilized on the nanoparticle. In some embodiments, the kits may further include instructions for combining the enzyme and the nanoparticles to form an enzyme composition. In some embodiments, the kits may further include instructions for using the composition.

DETAILED DESCRIPTION

Figure 1:
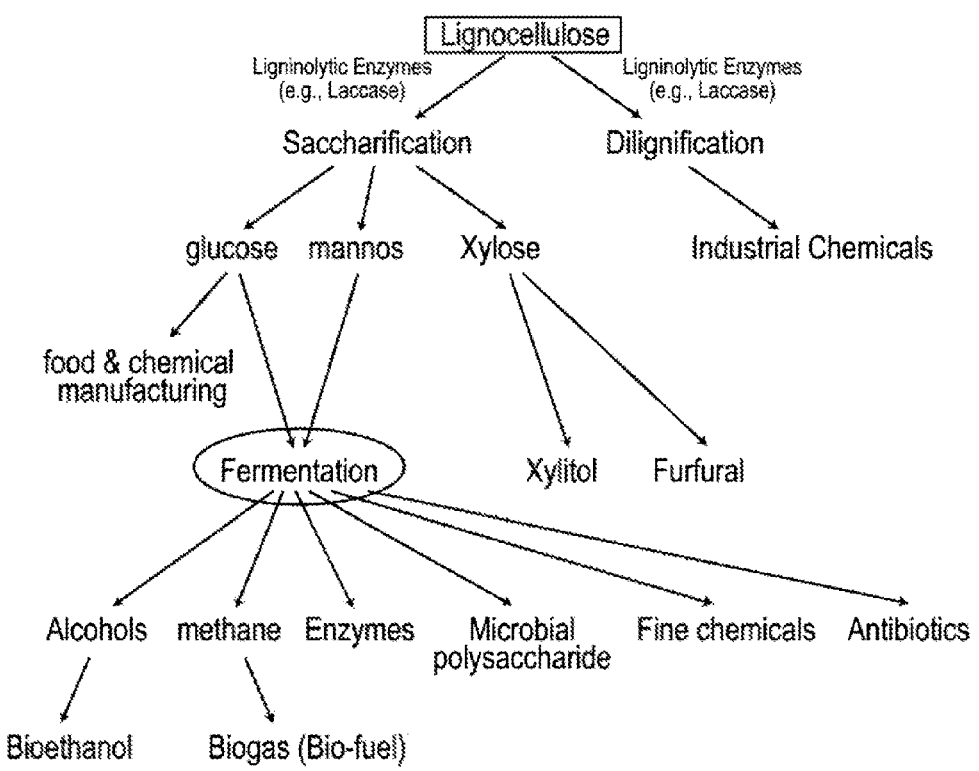
FIG. 1 is a schematic diagram showing exemplary use of the compositions of the present technology comprising a laccase enzyme and nanoparticles comprising cuprous oxide in the degradation of lignocellulosic materials and the subsequent use of the degradation products.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Disclosed herein are compositions and methods related to the manufacture and use of stabilized laccase enzymes. In some embodiments, the enzyme compositions and methods disclosed herein include (1) laccase enzyme; and (2) at least one nanoparticle comprising cuprous oxide, wherein the enzyme is not immobilized on the nanoparticle. Typically, the nanoparticle comprising cuprous oxide is in contact with the enzyme.

In some embodiments, the composition includes at least one nanoparticle comprising magnesium chloride, manganese chloride, or calcium chloride and at least one laccase enzyme in contact with the nanoparticle comprising magnesium chloride, manganese chloride, or calcium chloride in which the enzyme is not immobilized on the nanoparticle.

For the purposes of this disclosure and unless otherwise specified, "a" or "an" means "one or more."

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein a "treated" laccase enzyme refers to laccase enzyme that is mixed with, incubated with, in contact with, or that has been contacted with, a nanoparticle comprising cuprous oxide, magnesium chloride, manganese chloride, or calcium chloride. In some embodiments, the enzyme is in contact with at least a portion of at least one nanoparticle. Additionally or alternatively, in some embodiments, the enzyme is in contact with the nanoparticle; or cuprous oxide, magnesium chloride, manganese chloride, or calcium chloride; or both. The contact can be by various mechanisms, such as by hydrogen bonding, van der waals force, etc.

As used here in "substrate" in the context of laccase enzyme refers to a molecule or a group of molecules upon which an enzyme acts. Enzymes catalyze chemical reactions involving the substrate(s). The substrate binds with the laccase enzyme active site, and an enzyme-substrate complex is formed. The substrate is transformed into one or more products, which are then released from the active site.

In some embodiments, the substrate comprises a phenolic hydroxyl group. In some embodiments, the substrate comprises an azo group. In some embodiments, the substrate comprises syringaldazine, congo red, cotton blue, bromophenol blue, malachite green. In some embodiments, the substrate comprises ortho and/or paradiphenols, aminophenols, polyphenols, polyamines, lignins and/or aryl diamines. In some embodiments, the substrate comprises a textile, wool, biocomposite, wastewater, paper, wood pulp, soil, animal feed, food, beverage, herbicide, pesticide, dye, pigment, or combinations thereof. In some embodiments, the substrate comprises wood pulp comprising lignin.

As used herein the term "enhanced activity" or "increased activity" in the context of laccase enzyme refers to an enhanced or increased number of moles of substrate converted per unit time for a laccase enzyme treated with nanoparticles comprising cuprous oxide, magnesium chloride, manganese chloride, or calcium chloride as compared to a laccase enzyme that is not treated with such nanoparticles.

In some embodiments, the enhanced activity or increased activity of a laccase enzyme refers to an increase in the maximum reaction velocity ($V_{max}$), and/or an increase in turnover number i.e., the number of substrate molecule each enzyme site converts to product per unit time, and/or an increase in substrate affinity for example, decrease in Michaelis Constant ($K_m$). In some embodiments, the enhanced activity or increased activity of a laccase enzyme refers to a decrease in the activation energy ($E_a$).

As used herein "enhanced half life" or "increased half life" in the context of laccase enzyme refers to enhancement or increase in the amount of time the laccase enzyme can retain 50% of its activity as compared to the enzyme activity at a reference temperature.

In some embodiments, an elevated temperature in the context of laccase enzyme (for example, for laccase enzyme activity) can be from about 40° C. to about 120° C., from about 50° C. to about 110° C., or from about 50° C. to about 100° C. In some embodiments, an elevated temperature in the context of laccase enzyme can be about 40° C., 42° C., 45° C., 50° C., 55° C., 60° C., 65° C., 70° C., 75° C., 80° C., 85° C., 90° C., 95° C., 100° C., 105° C., 110° C., or ranges between any two of these values. In some embodiments, a reference temperature in the context of laccase enzyme can be from about 20° C. to about 60° C., or from about 30° C. to about 50° C., from about 40° C. to about 50° C. In some embodiments, the reference temperature in the context of laccase enzyme can be about 20° C., 25° C., 30° C., 35° C., 37° C., 40° C., 42° C., 45° C., 47° C., 48° C., 50° C., or ranges between any two of these values.

As used herein "enhanced thermal stability" or "increased thermal stability" in the context of laccase enzyme refers to enhancement or increase in structural and functional integrity, at a given temperature, of laccase enzyme treated with nanoparticles comprising cuprous oxide, magnesium chloride, manganese chloride, or calcium chloride as compared to a laccase enzyme that is not treated with such nanoparticles.

In some embodiments, the terms enhanced thermal stability or increased thermal stability refers to increased resistance to heat denaturation of the laccase enzyme. In some embodiments, the terms enhanced thermal stability or increased thermal stability indicates that the laccase enzyme (for example, a laccase enzyme treated with nanoparticles comprising cuprous oxide, magnesium chloride, manganese chloride, or calcium chloride) has an enhanced half life or an increased half life at a given temperature (for example, as compared to an untreated laccase enzyme). In some embodiments, the terms enhanced thermal stability or increased thermal stability refers to increase in the deactivation energy ($E_d$) of laccase enzyme treated with nanoparticles comprising cuprous oxide as compared to a laccase enzyme that is not treated with such nanoparticles.

In some embodiments, the terms enhanced thermal stability or increased thermal stability of laccase enzyme can be determined at a temperature range from about 40° C. to about 120° C., from about 50° C. to about 110° C., or from about 50° C. to about 100° C. In some embodiments, the elevated temperature in the context of laccase enzyme can be about 40° C., 42° C., 45° C., 50° C., 55° C., 60° C., 65° C., 70° C., 75° C., 80° C., 85° C., 90° C., 95° C., 100° C., 105° C., 110° C., or ranges between any two of these values. In some embodiments, the thermal stability of laccase enzyme can be determined at a temperature from about 20° C. to about 60° C., or from about 30° C. to about 50° C., from about 40° C. to about 50° C. In some embodiments, the reference temperature in the context of laccase enzyme can be about 20° C., 25° C., 30° C., 35° C., 37° C., 40° C., 42° C., 45° C., 47° C., 48° C., 50° C., or ranges between any two of these values.

As used herein, "decreased pH dependency" in the context of laccase enzyme refers to the characteristic of an enzyme (for example, a laccase enzyme treated with nanoparticles comprising cuprous oxide, magnesium chloride, manganese chloride, or calcium chloride) to exhibit greater activity at a given pH than a comparable enzyme (for example, an untreated laccase enzyme). In some embodiments, an enzyme exhibiting a decreased pH dependency (for example, a treated laccase enzyme) retains 10%, 20%, 30%, 40%, 50%, 60%, 70%, 80%, 90% or 100% of its activity at a given pH, while an enzyme that does not exhibit decreased pH dependency (for example, a "control" or untreated enzyme) exhibits a lower % activity at the same pH. In some embodiments, an enzyme exhibiting a decreased pH dependency includes a laccase enzyme which retains 50% of its activity when treated with nanoparticles comprising cuprous oxide, magnesium chloride, manganese chloride, or calcium chloride at a pH range from about 2-13, from about 3-13, from about 3-11, or from about 3-10. In some embodiments, an enzyme exhibiting a decreased pH dependency includes a laccase enzyme which retains 50% of its activity when treated with nanoparticles comprising cuprous oxide, magnesium chloride, manganese chloride, or calcium chloride at a pH of about 2, about pH 3, about pH 4, about pH 5, about pH 6, about pH 7, about pH 8, about pH 9, about pH 10, about pH 11, about pH 12, or about pH 13.

In some embodiments, a reference pH value in the context of laccase enzyme activity can be about pH 7, pH 8, pH 9, or pH 10.

As used herein, "stabilized" in the context of laccase enzyme refers to a laccase enzyme having one or more of enhanced activity or increased activity; enhanced activity or increased activity at increased or elevated temperature, enhanced thermal stability or increased thermal stability; enhanced half life or increased half life; and/or decreased pH dependency.

I. Nanoparticles

The nanoparticles provided in several illustrative embodiments described herein refer to any particle in which the largest dimension is in the nanometer range, and/or in the instance wherein the composition contains a plurality of nanoparticles, the dimension described herein can refer to an average of the individual dimensions of the plurality of the nanoparticles. For example, in some embodiments, the nanoparticle has a largest dimension that is less than 1000 nm, for example, about 999 nm, about 900 nm, about 800 nm, about 700 nm, about 600 nm, about 500 nm, about 400 nm, about 350 nm, about 300 nm, about 200 nm, about 100 nm, or ranges between any two of these values. Additionally or alternatively, in some embodiments, the largest dimension of the nanoparticle is, for example, about 100 nm, and in further examples, about 90 nm, about 80 nm, about 70 nm, about 60 nm, about 50 nm, about 25 nm, about 20 nm, about 10 nm, about 5 nm, about 3 nm, about 2 nm, about 1 nm or less, or ranges between any two of these values.

As noted above, the dimension can refer to, for example, the largest dimension of the particle. Additionally or alternatively, the dimension can refer to the smallest dimension of the particle. The particle can have any shape. For example, the nanoparticles in some embodiments can refer to particles that are at least substantially spherical. Additionally or alternatively, nanoparticles can have a shape that is an ellipsoid, cube, cylindrical, or an irregular shape. Depending on the shape, the dimension described herein can refer to any of diameter, radius, width, length, height, diagonal, and the like. Also, in the instance wherein the composition contains a plurality of nanoparticles, the dimension described herein can refer to an average of the individual dimensions of the plurality of the nanoparticles. For example, in some embodiments, the average of the individual dimensions of the plurality of nanoparticles is about 1000 nm, about 999 nm, about 900 nm, about 800 nm, about 700 nm, about 600 nm, about 500 nm, about 400 nm, about 300 nm, about 200 nm, about 100 nm, or ranges between any two of these values. Additionally or alternatively, in some embodiments, the average of the individual dimensions of the plurality of nanoparticles is, for example, about 100 nm, about 90 nm, about 80 nm, about 70 nm, about 60 nm, about 50 nm, about 25 nm, about 20 nm, about 10 nm, about 5 nm, about 3 nm, about 2 nm, about 1 nm, or ranges between any two of these values.

In some embodiments, the nanoparticle has a shape that is at substantially spherical and a diameter of about 2 nm to about 500 nm, about 10 nm to about 500 nm, about 25 nm to about 500 nm, about 50 nm to about 400 nm, about 100 nm to about 400 nm, about 80 nm to about 100 nm.

In some embodiments, the nanoparticles comprise cuprous oxide. In some embodiments, the nanoparticles comprise magnesium chloride, manganese chloride, or calcium chloride.

II. Enzyme

In some embodiments provided herein, at least one laccase enzyme in contact with or treated with a nanoparticle comprising cuprous oxide, magnesium chloride, manganese chloride, or calcium chloride in which the enzyme is not immobilized on the nanoparticle.

In some embodiments, the laccase enzyme is provided as a composition. In some embodiments, the laccase enzyme in the composition that is in contact with or treated with a nanoparticle comprising cuprous oxide, magnesium chloride, manganese chloride, or calcium chloride is more stabilized as compared to the same enzyme not treated with or not in contact with a nanoparticle comprising cuprous oxide, magnesium chloride, manganese chloride, or calcium chloride. In some embodiments, the enzyme in the composition exhibits an increased activity towards a substrate, is more thermostable, has an increased activity at a higher temperature, has a longer half-life, and/or decreased pH dependency as compared to the same enzyme that is not in contact with the nanoparticle comprising cuprous oxide, magnesium chloride, manganese chloride, or calcium chloride.

In some embodiments, the enzyme in the composition exhibits an increased activity towards a substrate as compared to the same enzyme that is not in contact with or treated with the nanoparticle comprising cuprous oxide, magnesium chloride, manganese chloride, or calcium chloride.

Additionally or alternatively, in some embodiments, the laccase enzyme in the composition is more thermostable as compared to the same enzyme that is not in contact with the nanoparticle comprising cuprous oxide, magnesium chloride, manganese chloride, or calcium chloride. Additionally or alternatively, in some embodiments, the laccase enzyme in the composition has an increased activity at a higher temperature as compared to the same enzyme that is not in contact with or treated with the nanoparticle comprising cuprous oxide, magnesium chloride, manganese chloride, or calcium chloride. In some embodiments, the laccase enzyme in the composition has an increased activity at a higher temperature and is more thermostable as compared to the same enzyme that is not in contact with or treated with the nanoparticle comprising cuprous oxide, magnesium chloride, manganese chloride, or calcium chloride. In some embodiments, the laccase enzyme in the composition has an increased activity at a temperature of about 70° C. to about 100° C. as compared to the same enzyme that is not in contact with or treated with the nanoparticle comprising cuprous oxide, magnesium chloride, manganese chloride, or calcium chloride. In some embodiments, the laccase enzyme in the composition has an increased activity at a temperature of about 70° C. to about 100° C. and is more thermostable as compared to the same enzyme that is not in contact with the nanoparticle comprising cuprous oxide, magnesium chloride, manganese chloride, or calcium chloride.

In some embodiments, the enzyme in the composition has a longer half-life as compared to the same enzyme that is not in contact with or treated with the nanoparticle comprising cuprous oxide, magnesium chloride, manganese chloride, or calcium chloride.

In some embodiments, the enzyme in the composition has a decreased pH dependency as compared to the same enzyme that is not in contact with or treated with the nanoparticle comprising cuprous oxide, magnesium chloride, manganese chloride, or calcium chloride. In some embodiments, the enzyme in the composition can act on a substrate at pH 3-12. In some embodiments, the enzyme in the composition can act on a substrate at pH 8-10.

In some embodiments, the laccase enzyme in the composition is a copper-containing oxidase enzyme that can be found in many plants, fungi, and microorganisms. Typically, laccase enzymes catalyze the oxidation of wide variety of organic and inorganic substrates. Non-limiting examples of such substrates include: mono-, di-, poly phenols, amino phenols, amino phenols, methoxy phenols, aromatic amines, ascorbates.

In some embodiments, the substrate comprises an azo group. In some embodiments, the substrate comprises syringaldazine, congo red, cotton blue, bromophenol blue, malachite green, methyl orange or substrates comprising ortho and paradiphenols, aminophenols, polyphenols, polyamines, lignins and/or aryl diamines. In some embodiments, the substrate comprises a textile, wool, biocomposite, wastewater, paper, wood pulp, soil, animal feed, food, beverage, herbicide, pesticide, dye, pigment or combinations thereof. In some embodiments, the substrate comprises wood pulp comprising lignin.

The compositions of the present technology (for example, laccase enzymes in contact with nanoparticles comprising cuprous oxide, magnesium chloride, manganese chloride, or calcium chloride) are useful in the transformation of a wide variety of phenolic compounds including, without limitation, polymeric lignin and humic substances. Additionally or alternatively, in some embodiments, the composition is useful for the transformation or immobilization of xenobiotic compounds.

The laccase enzymes of the present technology can be derived from a variety of bacterial, fungal or recombinant sources. In some embodiments, the enzyme is derived from one or more of *Escherichia coli* AKL2, *Pseudomonas marginalis*, *Azospirillum lipoferum*, *Streptomyces* sp., *Rhus vernicifera*, *Mycobacterium tuberculosis*, *Escherichia coli*, *Caulobacter crescentus*, *Pseudomonas syringae*, *Bordetella pertussis*, *Xanthomonas campestris*, *Pseudomonas aeruginosa*, *Mycobacterium avium*, *Pseudomonas putida*, *Rhodobacter capsulatus*, *Yersinia pestis*, *Campylobacter jejuni*, *Aquifex aeolicus*, *Physisporinus rivulosus*, *Melanocarpus albomyces*, *Agaricus blazei*, *Trametes versicolor*, *Pycnoporus sanguineus*, and/or *Basidiomycota* sp.

Additionally or alternatively, in some embodiments, the enzyme is purified from *Escherichia coli* AKL2, *Pseudomonas marginalis*, *Azospirillum lipoferum*, *Streptomyces* sp., *Rhus vernicifera*, *Mycobacterium tuberculosis*, *Escherichia coli*, *Caulobacter crescentus*, *Pseudomonas syringae*, *Bordetella pertussis*, *Xanthomonas campestris*, *Pseudomonas aeruginosa*, *Mycobacterium avium*, *Pseudomonas putida*, *Rhodobacter capsulatus*, *Yersinia pestis*, *Campylobacter jejuni*, *Aquifex aeolicus*, *Physisporinus rivulosus*, *Melanocarpus albomyces*, *Agaricus blazei*, *Trametes versicolor*, *Pycnoporus sanguineus*, and/or *Basidiomycota* sp.

In some embodiments, laccase is secreted into the culture media by one or more of the above microorganisms and the enzyme is purified from the culture media comprising secreted laccase. In one embodiment, laccase is secreted into the culture media by *Escherichia coli* AKL2, and the enzyme is purified from the media. Nucleic acid sequence of *Escherichia coli* AKL2 is deposited in GenBank (Accession No. JQ965012).

Exemplary amino acid sequences of laccase enzyme include but are not limited to the enzyme from *Trametes versicolor* (GenBank Accession Number: CAA77015), Basidiomycete PM1 (GenBank Accession Number: CAA78144), *Escherichia coli* Laccase CueO (GenBank Accession Number: 2FQG_A, 2FQF_A, 2FQE_A), *Escherichia coli* W multicopper oxidase (laccase) (GenBank Accession Number: ADT73670), *Streptomyces* sp. C1 (GenBank Accession Number: AEP17492), *Streptomyces griseus* XylebKG-1 Multi-copper polyphenol oxidoreductase, laccase (GenBank Accession Number: EGE45048). Exemplary amino acid sequences of laccase enzyme from various sources are listed as SEQ ID NOs: 4, 6, 8, 10, 12, 14, 16; and their corresponding nucleic acid sequences are listed as SEQ ID NOs: 5, 7, 9, 11, 13, 15, and 17, respectively.

In some embodiments, the enzyme can be an enzyme in a natural form (for example, native enzyme) or a synthetic form, such as a recombinant enzyme. Additionally or alternatively, in some embodiments, the enzyme is recombinantly modified to comprise a non-heterologous peptide tag.

Exemplary non-heterologous peptide tags include but are not limited to (His)$_6$ tag, glutathione-S-transferase tag (GST), peptide fragments of human proto-oncoprotein MYC (for example, N-ILKKATAYIL-C(SEQ ID NO: 1), N-EQKLISEEDL-C (SEQ ID NO: 2)), peptide fragments of influenza protein haemagglutinin (HA) for example, N-YPYDVP-C (SEQ ID NO: 3).

In some embodiments, the laccase enzyme can be purified from *Pseudomonas marginalis*. For example, in one non-limiting example, the *Pseudomonas marginalis* bacteria was isolated from termite soil. Bacterial laccase enzyme was purified from the bacteria by two consecutive processes. First, by ion exchange chromatography (CM Sepharose) was employed. Second, gel filtration chromatography (Sephadex G-75) was used to further purify the enzyme. The purified enzymes are then treated with nanoparticles comprising cuprous oxide, magnesium chloride, manganese chloride, or calcium chloride, resulting in a treated enzyme composition with enhanced activity, thermostability and a decreased pH dependence. The treated enzyme composition can then be used to treat various substrates.

In some embodiments, the laccase enzyme can be purified from *Escherichia coli*. In one example, laccase was purified from a 100-ml *E. coli* culture in Luria broth. Cell-free supernatant was mixed with 10 ml CM-Sepharose pre-equilibrated with Tris-HCl buffer (25 mM, pH 8) and kept at 4° C. overnight. After leaving the mixture overnight, 10 ml of the mixture was loaded onto a column (10 ml bed volume). Bound compounds were eluted with Tris-HCl buffer (25 mM, pH 8) containing 0-1 M NaCl. Fractions of 1 ml were collected and those showing laccase activity were concentrated using a Macrosep 10 K unit and loaded onto a glass column packed with Sephadex G-75 (bed volume 30 ml) and equilibrated with the same Tris-HCl buffer. Elution of the proteins was done using Tris-HCl buffer (25 mM, pH 8). The eluted proteins were analyzed by 12% SDS poly-acrylamide gel electrophoresis (PAGE). Protein markers and protein bands were stained by silver staining.

In some embodiments, reactions with laccase enzyme of the present technology (for example, laccase enzyme treated with nanoparticle comprising cuprous oxide, magnesium chloride, manganese chloride, or calcium chloride) can be carried out at a temperature from about 30° C. to about 120° C., from about 40° C. to about 110° C., from about 40° C. to about 100° C., from about 50° C. to about 100° C., from about 50° C. to about 90° C. In some embodiments, the reactions with laccase enzyme of the present technology can be carried out at a temperature of about: 40° C., 50° C., 55° C., 60° C., 65° C., 70° C., 75° C., 80° C., 85° C., 90° C., 95° C., 100° C., 105° C., 110° C., or ranges between any two of these values.

In some embodiments, the reactions with laccase enzyme of the present technology (for example, laccase enzyme treated with nanoparticle comprising cuprous oxide, magnesium chloride, manganese chloride, or calcium chloride) can be carried out at pH: from about 3 to about 12, from about 6 to about 12, from about 8 to about 10. In some embodiments, the reactions with laccase enzyme of the present technology can be carried out at pH of about: 3, 4, 5, 6, 7, 8, 9, 10, 11, 12, or ranges between any two of these values. In some embodiments, the reactions with laccase enzyme can be carried out at pH of about 9.

In some embodiments, the concentration of cuprous ion or nanoparticles in the composition comprising at least one laccase enzyme in contact with a nanoparticle comprising cuprous oxide is from about 0.05 mM to about 0.15 mM. In some embodiments, the concentration of cuprous ion or nanoparticles in the composition comprising at least one laccase enzyme in contact with a nanoparticle comprising cuprous oxide is 0.1 mM.

III. Measuring Laccase Enzyme Activity

Laccase enzyme activity can be measured by any readily available technique. For example, in some embodiments, laccase activity can be measured spectrophotometrically using exemplary substrates such as 2,2'-azino-bis(3-ethyl-benzothiazoline-6-sulphonic acid) or ABTS, syringaldazine, 2,6-dimethoxyphenol, and/or dimethyl-p-phenylenedi-amine. Additionally or alternatively, in some embodiments, laccase activity can also be monitored with an oxygen sensor, as the oxidation of the substrate is paired with the reduction of oxygen to water. Exemplary method of purify-ing and assaying the laccase enzyme is disclosed by Dia-mantidis et al., (Purification and characterization of the first bacterial laccase in the rhizospheric bacterium *Azospirillum lipoferum*. Soil Biology & Biochemistry 2000; 32: 919-927.

In some embodiments, laccase enzyme activity is mea-sured using syringaldazine assay. In an exemplary reaction, appropriate dilution of 1 ml supernatant is added to 3 ml of 25 mM Tris-HCl buffer, pH: 8.5, and then 2 ml substrate syringaldazine (solution in methanol and 1:2 dilution by Dioxan) is added to make a total assay system of 5 ml. The change in color from straw yellow to dark pink or violet indicates laccase activity. The reaction is typically moni-tored by measuring the absorbance at 525 nm. Additionally or alternatively, in some embodiments, laccase activity can be characterized by kinetic parameters, including $K_m$, $V_{max}$, and the activation energy, as described below. In some embodiments, the enzyme activity can be determined by the bleaching of ramie fiber. For example, in some embodi-ments, a piece of ramie fiber is incubated in a laccase secreting bacterial culture medium for a fixed amount of time, for example, for 48 hours, and the enzyme activity is determined by the degree of bleaching.

IV. Treatment of Enzymes with Nanoparticles Comprising Cuprous Oxide, Magnesium Chloride, Manganese Chloride, or Calcium Chloride Provided herein are methods of treating laccase enzyme with nanoparticles. In some embodiments, the treatment method includes combining to form a mixture: i) nanopar-ticles comprising cuprous oxide, magnesium chloride, man-ganese chloride, or calcium chloride; and ii) laccase enzyme; under conditions in which the enzyme is in contact with the nanoparticles and the enzyme is not immobilized on the nanoparticle.

In some embodiments, the mixture comprising the laccase enzyme and the nanoparticles comprising cuprous oxide, magnesium chloride, manganese chloride, or calcium chlo-ride can be incubated by any suitable incubation techniques. Additionally or alternatively, in some embodiments, incu-bation conditions can vary depending on the materials being incubated. For example, in one embodiment, the mixture is incubated at about 30° C. to about 100° C. In some embodi-ments, the mixture is incubated at about 40° C., about 50° C., about 55° C., about 60° C., about 65° C., about 70° C., about 75° C., about 80° C., about 85° C., about 90° C., or ranges between any two of these values. In another embodi-ment, the incubation can be carried out for a period of about 10 minutes to about 10 hours—for example, about 10 minutes, 20 minutes, 30 minutes, 40 minutes, 50 minutes, 1 hour, 2 hours, 3 hours, 4 hours, 5 hours, 6 hours, 7 hours, 8 hours, 9 hours, 10 hours, or from about 2 hours to about 5 hours, about 3 to about 4 hours. In some embodiments, the incubation can be carried out at pH from about 3 to about 12. In some embodiments, the incubation can be carried out at about pH: 3, 4, 5, 6, 7, 8, 9, 10, 11, 12, or ranges between any two of these values. In some embodiment, the incubation can be carried out at pH of about 8.5. In some embodiment, the incubation can be carried out at pH of about 8.5 at 50° C. for 15 min. In some embodiment, the incubation can be carried out at pH of about 9. In some embodiment, the incubation can be carried out at pH of about 9 at 80° C. for 120 min. In some embodiments, the mixture comprising the laccase enzyme and the nanoparticles comprising cuprous oxide, magnesium chloride, manganese chloride, or calcium chloride are not incubated prior to treating a substrate.

In some embodiments of the method, the enzyme comprises recombinant enzyme. In some embodiments, the enzyme treatment can include purifying the laccase enzyme (for example, from a bacterial or fungal source) before it is combined into the mixture (for example, before it is combined with nanoparticle comprising cuprous oxide, magnesium chloride, manganese chloride, or calcium chloride, or before it is combined with nanoparticles comprising cuprous oxide, magnesium chloride, manganese chloride, or calcium chloride and a substrate).

In some embodiments, the enzyme is derived from a microorganism, such as a bacteria or fungus. For example, in some embodiments, the enzyme derived from one or more of *Pseudomonas marginalis, Azospirillum lipoferum, Streptomyces* sp., *Rhus vernicifera, Mycobacterium tuberculosis, Escherichia coli, Caulobacter crescentus, Pseudomonas syringae, Bordetella pertussis, Xanthomonas campestris, Pseudomonas aeruginosa, Mycobacterium avium, Pseudomonas putida, Rhodobacter capsulatus, Yersinia pestis, Campylobacter jejuni, Aquifex aeolicus, Physisporinus rivulosus, Melanocarpus albomyces, Agaricus blazei, Trametes versicolor, Pycnoporus sanguineus,* and/or *Basidiomycota* sp.

In some embodiments, the enzyme is purified from *Pseudomonas marginalis, Azospirillum lipoferum, Streptomyces* sp., *Rhus vernicifera, Mycobacterium tuberculosis, Escherichia coli, Caulobacter crescentus, Pseudomonas syringae, Bordetella pertussis, Xanthomonas campestris, Pseudomonas aeruginosa, Mycobacterium avium, Pseudomonas putida, Rhodobacter capsulatus, Yersinia pestis, Campylobacter jejuni, Aquifex aeolicus, Physisporinus rivulosus, Melanocarpus albomyces, Agaricus blazei, Trametes versicolor, Pycnoporus sanguineus,* and/or *Basidiomycota* sp. In some embodiments, the enzyme is recombinantly derived.

In some embodiments, the enzyme is recombinantly modified to further comprise a non-heterologous peptide tag. Exemplary non-heterologous peptide tags include but are not limited to (His)$_6$ tag, glutathione-S-transferase tag (GST), peptide fragments of human proto-oncoprotein MYC (for example, N-ILKKATAYIL-C(SEQ ID NO: 1), N-EQKLISEEDL-C(SEQ ID NO: 2)), peptide fragments of Influenza protein haemagglutinin (HA) for example, N-YPYDVP-C (SEQ ID NO: 3).

Alternatively, unpurified enzyme can be combined with the nanoparticles comprising cuprous oxide, magnesium chloride, manganese chloride, or calcium chloride (or nanoparticles and substrate) to form the mixture.

In some embodiments, treatment of enzymes with nanoparticles comprising cuprous oxide, magnesium chloride, manganese chloride, or calcium chloride alters the properties of an enzyme. In some embodiments, the laccase enzyme treated with nanoparticles comprising cuprous oxide, magnesium chloride, manganese chloride, or calcium chloride is more stabilized as compared to the same enzyme that is not in contact with or not treated with the nanoparticle comprising cuprous oxide, magnesium chloride, manganese chloride, or calcium chloride.

In some embodiments, the treatment of laccase enzyme with nanoparticles comprising cuprous oxide, magnesium chloride, manganese chloride, or calcium chloride results in improved thermal stability, enzyme activity, increased activity at a higher (or elevated) temperature, and/or decreased pH dependency. In some embodiments, the treatment of laccase enzyme with the nanoparticles can increase detergent tolerance relative to laccase enzyme without nanoparticles.

For example, in some embodiments, a laccase enzyme treated with nanoparticles comprising cuprous oxide, magnesium chloride, manganese chloride, or calcium chloride can have an increased activity as compared to the same enzyme that is not in contact with the nanoparticle comprising cuprous oxide, magnesium chloride, manganese chloride, or calcium chloride. In some embodiments, the increase in activity can be at least about 5%, at least about 10%, at least about 15%, at least about 20%, at least about 25%, at least about 30%, at least about 35%, at least about 40%, at least about 45%, at least about 50%, at least about 55% at least about 60%, at least about 70%, at least about 80%, at least about 90%, at least about 100%, at least about 200%, at least about 400%, at least about 600%, at least about 800%, or at least about 1000% greater than an enzyme not in contact with the nanoparticle comprising cuprous oxide, magnesium chloride, manganese chloride, or calcium chloride. In some embodiments, the increase can be at least an order of magnitude higher, such as 10 times, 20 times, 30 times, 40 times, 50 times or more higher than an enzyme not in contact with the nanoparticle comprising cuprous oxide, magnesium chloride, manganese chloride, or calcium chloride.

Additionally, or alternatively, in some embodiments, the laccase enzyme treated with nanoparticles comprising cuprous oxide, magnesium chloride, manganese chloride, or calcium chloride exhibits more thermal stability as compared to the same enzyme that is not treated with the nanoparticle comprising cuprous oxide, magnesium chloride, manganese chloride, or calcium chloride. For example, in some embodiments, treatment with nanoparticles comprising cuprous oxide, magnesium chloride, manganese chloride, or calcium chloride can increase the thermal stability. Thermal stability can be measured and described via several metrics. For example, an increase in thermal stability can refer to an enzyme retaining its activity after being exposed to an elevated temperature for a period of time. For example, in some embodiments, the treated enzyme retains activity after being exposed to an elevated temperature for at least 2 hours—for example, at least 3 hours, at least 4 hours, at least 5 hours, at least 6 hours, at least 8 hours, at least 10 hours, or ranges between any two of these values. In some embodiments, the elevated temperature refers to a temperature higher than a room temperature—for example, at least 30° C., at least 37° C., at least 40° C., at least 45° C., at least 50° C., at least 55° C., at least 60° C., at least 65° C., at least 70° C., at least 75° C., at least 80° C., at least 85° C., at least 90 C., at least 95° C., at least 100° C., at least 105° C., at least 110° C., at least 115° C., at least 120° C. or higher.

Additionally or alternatively, in some embodiments, the laccase enzyme in contact with nanoparticles comprising cuprous oxide, magnesium chloride, manganese chloride, or calcium chloride can have an increased activity at a higher (or elevated) temperature as compared to the same enzyme that is not in contact with the nanoparticle comprising cuprous oxide, magnesium chloride, manganese chloride, or calcium chloride. For example, in some embodiments the increase can be at least about 5%, at least about 10%, at least about 15%, at least about 20%, at least about 25%, at least about 30%, at least about 35%, at least about 40%, at least about 45%, at least about 50%, at least about 55% at least about 60%, at least about 70%, at least about 80%, at least about 90%, at least about 100%, at least about 200%, at least about 400%, at least about 600%, at least about 800%, or at least about 1000% greater than an enzyme not in contact with the nanoparticle comprising cuprous oxide, magnesium chloride, manganese chloride, or calcium chloride. In some embodiments, the increase can be at least an order of magnitude higher, such as 10 times, 20 times, 30 times, 40 times, 50 times or more higher than an enzyme not in contact with the nanoparticle comprising cuprous oxide, magnesium chloride, manganese chloride, or calcium chloride.

In some embodiments, the elevated temperature refers to a temperature higher than a room temperature—for example, at least 30° C., at least 37° C., at least 40° C., at least 45° C., at least 50° C., at least 55° C., at least 60° C., at least 65° C., at least 70° C., at least 75° C., at least 80° C., at least 85° C., at least 90° C., at least 95° C., at least 100° C., at least 105° C., at least 110° C., at least 115° C., at least 120° C. or higher. In some embodiments, the elevated temperature refers to a temperature of about 40° C., about 45° C., about 50° C., about 55° C., about 60° C., about 65° C., about 70° C., about 75° C., about 80° C., about 85° C., about 90 C., about 95° C., about 100° C., about 105° C., about 110° C., about 115° C., about 120° C., or ranges between any two of these values.

In some embodiments, a laccase enzyme in contact with nanoparticles comprising cuprous oxide, magnesium chloride, manganese chloride, or calcium chloride can have a longer half-life ($t_{1/2}$) as compared to the same enzyme that is not in contact with nanoparticles comprising cuprous oxide, magnesium chloride, manganese chloride, or calcium chloride. In some embodiments, the increase in half-life is at least about 5%, at least about 10%, at least about 15%, at least about 20%, at least about 25%, at least about 30%, at least about 35%, at least about 40%, at least about 45%, at least about 50%, at least about 55% at least about 60%, at least about 70%, at least about 80%, at least about 90%, at least 100%, at least 200%, at least 400%, at least 600%, at least 800%, at least 1000% longer as compared to the same enzyme that is not in contact with nanoparticles comprising cuprous oxide, magnesium chloride, manganese chloride, or calcium chloride. In some embodiments, the increase can be at least an order of magnitude higher, such as 10 times, 20 times, 30 times, 40 times, 50 times, longer.

In some embodiments, the laccase enzyme in contact with nanoparticles comprising cuprous oxide, magnesium chloride, manganese chloride, or calcium chloride can have an increased detergent tolerance as compared to the same enzyme that is not in contact with the nanoparticle comprising cuprous oxide, magnesium chloride, manganese chloride, or calcium chloride. For example, the increase in detergent tolerance can be at least about 5%, at least about 10%, at least about 15%, at least about 20%, at least about 25%, at least about 30%, at least about 35%, at least about 40%, at least about 45%, at least about 50%, at least about 55% at least about 60%, at least about 70%, at least about 80%, at least about 90%, at least about 100%, at least about 200%, at least about 400%, at least about 600%, at least about 800%, or at least about 1000% greater than an enzyme not in contact with the nanoparticle comprising cuprous oxide, magnesium chloride, manganese chloride, or calcium chloride. In some embodiments, the increase can be at least an order of magnitude higher, such as 10 times, 20 times, 30 times, 40 times, 50 times or more higher than an enzyme not in contact with the nanoparticle comprising cuprous oxide, magnesium chloride, manganese chloride, or calcium chloride.

V. Select Illustrative Advantages of the Composition of the Present Technology Over Laccase Enzyme Alone There is an increasing demand to replace some traditional chemical processes with biotechnological processes involving microorganisms and enzymes which not only provide an economically viable alternative, but also are more environment-friendly.

The compositions of the present technology comprising laccase enzyme and nanoparticles comprising cuprous oxide, magnesium chloride, manganese chloride, or calcium chloride wherein the laccase enzyme is in contact with the nanoparticle and the enzyme is not immobilized on the nanoparticle has significant advantage over the laccase enzyme alone. The thermal stability, improved activity, and decreased pH dependency are advantageous in industrial processing conditions. Thermostability and increased catalytic activity are advantageous features as they increase the rate of activity and the shelf-life of the enzyme while decreasing energy consumption and costs when processing substrates. Further, improved enzymatic activity allows the processing of a larger volume of substrate. Additionally, the compositions of the present technology comprising laccase enzyme in contact with nanoparticles comprising cuprous oxide, magnesium chloride, manganese chloride, or calcium chloride can replace some traditional chemical processes. The compositions of the present technology comprising laccase enzyme in contact with nanoparticle comprising cuprous oxide, magnesium chloride, manganese chloride, or calcium chloride are not only economically viable alternative, but are also more environment friendly as compared to alternative chemical methods.

The decreased pH dependency of the compositions of the present technology comprising laccase enzyme in contact with nanoparticle comprising cuprous oxide, magnesium chloride, manganese chloride, or calcium chloride has significant advantages over laccase enzyme alone (untreated laccase enzyme) because untreated laccase enzyme has a more limited pH activity range.

The optimal pH values of untreated laccase vary depending on the substrate employed, molecular oxygen, and the enzyme itself. The different redox potentials of phenolic substrate can change the pH optima. Laccase enzyme catalyzes the oxidation of ortho and paradiphenols, aminophenols, polyphenols, polyamines, lignins and aryl diamines as well as some inorganic ions coupled to the reduction of molecular dioxygen to water. Textile dyes are generally different types of phenols and azo compounds. Advantageously, the composition of the present technology, comprising laccase enzymes in contact with nanoparticles comprising cuprous oxide, magnesium chloride, manganese chloride, or calcium chloride exhibits decreased pH dependency, and can thus act on a wider range of phenolic dyes as well as toxic substrates compared to untreated laccase enzymes.

VI. Illustrative Uses of the Compositions of the Present Technology

The composition of the present technology can be used for a variety of purposes. The composition provides robust catalytic alternatives for the breakdown of lignocellulosic materials under industrial processing temperature. In some embodiments, the composition of the present technology can be used for bio-bleaching of fibers, cottons in textile and paper industries in an environment friendly method. In some embodiments, the composition can be used for treatment of industrial wastewater containing phenolic, arylamine, diamine materials, and textile dye reagents. In some embodiments, the composition can be used for detoxification of industrial effluents. In some embodiments, the composition can be used for retting or bioscouring of natural bast fibers (for example, hemp and flax), and cotton fabric. In some embodiments, the composition can be used as an efficient tool for bio-remediation.

In some embodiments, the composition can be used to treat a substrate, the substrate comprises a phenolic hydroxyl group by contacting and/or incubating the substrate with a composition. In some embodiments, the substrate comprises an azo group. In some embodiments, the substrate comprises syringaldazine, congo red, cotton blue, bromophenol blue, malachite green. In some embodiments, the substrate comprises ortho and paradiphenols, aminophenols, polyphenols, polyamines, lignins and/or aryl diamines. In some embodiments, the substrate comprises a textile, wool, biocomposite, wastewater, paper, wood pulp, soil, animal feed, food, beverage, herbicide, pesticide, dye, pigment or combinations thereof. In some embodiments, the substrate comprises wood pulp comprising lignin.

In some embodiments, the substrate comprises dye or pigment, wherein the enzyme reacts with the dye or pigment and reduces the color of the substrate or decolorizes the substrate. In some embodiments, the substrate comprises a textile comprising a dye, wherein the enzyme reacts with the dye or pigment and reduces the color of the textile or decolorizes the textile. In some embodiments, the substrate comprises a beverage comprising phenolic compounds, wherein the enzyme reacts with the phenolic compound to reduce or remove browning or haze from the beverage. In some embodiments, the beverage is selected from fruit juice, beer, or wine.

In some embodiments, contacting the substrate is carried out at a temperature of about 30° C. to about 80° C. In some embodiments, contacting the substrate is carried out at a temperature of about 80° C. In some embodiments, contacting the substrate is carried out at a pH of about 3 to about 12. In some embodiments, contacting the substrate is carried out at a pH of about 9. In some embodiments, contacting the substrate is carried out from about 10 minutes to about 120 minutes.

A. Use of Enzyme Compositions of the Present Technology for Scouring

On an industrial scale chemical scouring is common, which improves water absorbency and whiteness of textiles by removing non-cellulosic substances from many natural fibers. Hazardous chemicals like soda-ash, oxalic acid, caustic soda, used in chemical scouring process, causes several environmental pollution as well as weaken the fiber strength.

Despite the interest in using laccase for bio-scouring processes, laccase enzymes currently in use suffers from a lack of scouring efficiency. Lack of scouring efficiency can arise from thermal instability and low activity of the enzyme. Thermal instability results in reduction of activity over time due to thermally induced changes in enzyme conformations. Higher temperature accelerates reduction in activity. Low activity limits the rate at which scouring can occur. Scouring efficiency can be increased by using compositions of the present technology, comprising laccase enzyme having increased thermostability and enzymatic activity as described herein.

B. Use of Enzyme Compositions in the Treatment of Industrial Effluents

Paper and pulp mills, molasses based-alcohol distilleries, tanneries, dye-making units and textiles are some of the major industries that produce and discharge highly colored effluents. Each of these industrial effluents creates some specific problem besides producing aesthetically unacceptable intense coloring of soil and water bodies. They block the passage of light to the lower depths of the aquatic system resulting in cessation of photosynthesis, leading to anaerobic conditions, which in turn result in the death of aquatic life causing foul smelling toxic waters.

The pollution problems due to the industrial effluents have increased in the recent years. The dyeing processes have, in general, a low yield and the percentage of the lost dye in the effluents can reach up to 50%. For example, textile dye effluents are complex, containing a wide variety of dyes, natural impurities extracted from the fibers and other products such as dispersants, leveling agents, acids, alkalis, salts and sometimes heavy metals. In general, the effluent is highly colored with high biological oxygen demand (BOD), suspended solids (SS), toxicity, and chemical oxygen demand (COD), it has a high conductivity and is alkaline in nature. The degradation products of the dyes are often carcinogenic. To meet stringent environmental regulations, the wastewaters have to be treated before their discharge to the environment. Most currently existing processes to treat dye wastewater are ineffective and not economical. Therefore, the development of processes based on the composition comprising laccase as described above, seems an attractive solution due to their potential in degrading dyes of diverse chemical structure, including synthetic dyes currently employed in the industry. The compositions of the present technology comprising laccase enzyme are able to detoxify wastewater containing chlorophenols by catalyzing their polymerization via radical coupling. The coupling products can be removed from the wastewater by precipitation. Chlorophenols can also cross-couple and precipitate with other phenols present in wastewater, which may enhance their removal efficiency.

C. Use of Enzyme Compositions in the Textile Industry

Denim Finishing

In the textile finishing industry, enzymatic degradation of indigo could have potential both in stone-wash process and for the treatment of dyeing effluents. Several steps are involved in the manufacture of denim garments between dyeing and the final stone-washing where excessive amounts of indigo are removed from the fabrics and discharged with the wastewater. The fabrics are partially bleached by a treatment with sodium hypochlorite, followed by neutralization and a rinsing step all causing substantial environmental pollution. The compositions of the present technology comprising the laccase enzyme are useful in denim finishing.

Cotton Bio-Bleaching

The purpose of cotton bleaching is to decolorize natural pigments and to confer a pure white appearance to the fibers. Mainly flavonoids are responsible for the color of cotton. The most common industrial bleaching agent is hydrogen peroxide. However, radical reactions of bleaching agents with the fiber can lead to a decrease in the degree of polymerization and, thus, to severe damage. Furthermore, a huge amount of water is needed to remove hydrogen peroxide from fabrics, which can cause problems in dyeing. Therefore, replacement of hydrogen peroxide by an enzymatic bleaching system would not only lead to better product quality due to less fiber damage but also to substantial savings on washing water needed for the removal of hydrogen peroxide.

The compositions of the present technology comprising laccase enzyme can enhance the bleaching effect on cotton fabrics. In addition, the short time of the enzymatic pretreatment sufficient to enhance fabric whiteness makes this bio-process suitable for continuous operations. Also, the composition of the present technology comprising laccase can improve the whiteness of cotton due to oxidation of flavonoids.

Other Uses in Textile Industries

The thermostable laccase enzymes of the present technology, with enhanced activity at higher temperatures and decreased pH dependency, are also useful in wool dyeing, rove scouring, anti-shrink treatment of wool, and dye synthesis.

In textile processing, laccase enzymes of the present technology can be used for improving the fabric whiteness in bleaching process, decolorization of dyed textile materials and colored effluent and scouring of fibers, wool dyeing, and wool anti-felting. Laccase enzymes of the present technology can be used to color wool fabric that was previously padded with hydroquinone. Laccase enzymes of the present technology can be used for wool dyeing. A dye bath can be prepared with a dye precursor (2,5-diaminobenzene-sulfonic acid), dye modifiers (catechol and resorcinol) and laccase, without any dyeing auxiliaries.

Laccase enzymes of the present technology is useful for reducing felting shrinkage of wool fabric. Increasing concentration of laccase can lead to a decrease in fabric shrinkage.

Laccase enzymes of the present technology can be used for roving treatment to improve yarn regularity. The advantage of the use of laccase in rove scouring is that the process is performed under mild reaction conditions resulting, thus, in an ecologically friendly process.

Laccase enzymes of the present technology can be used to form red azo dyes by the oxidative coupling of 3-methyl-2-benzothiazolinone hydrazone (MBTH) and phenols. Oxidation of ferulic acid by laccase in a biphasic hydro-organic medium leads to the production of stable yellow coloured products.

D. Use of the Composition in Paper Industries

The industrial preparation of paper requires separation and degradation of lignin in wood pulp. Environmental concerns compel the replacement of conventional and polluting chlorine-based delignification/bleaching procedures. The use of ligninolytic (lignin-degrading) enzymes (laccase) for the (pre)treatment of lignocellulosic raw material such as wood chips in pulping is referred to as biopulping. Biopulping is applicable to both mechanical and chemical pulps; its advantages include reduced refining energy or increased mill throughput in mechanical pulping, and enhanced paper strength properties, alleviated pitch problems, improved yield, and reduced environmental impact in mechanical and chemical pulping and papermaking. The compositions of the present technology comprising laccases and nanoparticles comprising cuprous oxide, magnesium chloride, manganese chloride, or calcium chloride have enhanced activity at higher temperatures and decreased pH dependency. The compositions can be used to activate the fiber bound lignin during manufacturing of the composites, thus, resulting in boards with good mechanical properties without toxic synthetic adhesives. Additionally or alternatively, the composition of the present technology comprising laccase are useful to graft various phenolics acid derivatives onto kraft pulp fibers.

E. Use of Enzyme Compositions in the Degradation of Lignocellulosic Materials

The compositions of the present technology comprising laccase are useful in degrading lignocellulosic materials. The compositions can be used, for example, to initiate a series of redox reactions, which degrade the lignin (or lignin-derived pollutants). The compositions can be used to oxidize aromatic compounds until the aromatic ring structure is cleaved, which can then be followed by additional degradation with other enzymes. The breakdown of lignocellulosic materials has wide variety of industrial applications.

Enzymatic hydrolysis of lignocellulosic materials is the first step for either digestion to biogas (methane) or fermentation to ethanol. Ethanol is an important renewable bio-fuel in terms of volume and market value. The demand for ethanol has a significant market, as ethanol is commonly used as a chemical feedstock or as an octane enhancer or petrol additive. Hence, the compositions of the present technology is useful in the production of ethanol from lignocellulosic materials.

Biogas is another energy source that is used as car fuel, or for production of heat or electricity. Pretreatment of lignocellulosic materials with the compositions of the present technology would degrade the lignocellulosic materials and help to produce ethanol and biogas.

Bioconversion of lignocellulosic breakdown wastes could make a significant contribution to the production of organic chemicals. FIG. 1 shows exemplary uses of the composition of the present technology in the breakdown of the lignocellulosic material and the use of the breakdown products in various applications.

In some embodiments, the composition of the present technology can be used to produce vanillin. Vanillin is an exemplary bio-product of lignin breakdown. The largest use of vanillin is as a flavoring, usually in sweet foods. It is used in the flavor industry, as a very important key note for many different flavors, especially creamy profiles. The ice cream and chocolate industries together comprise 75% of the market for vanillin as a flavoring, with smaller amounts being used in confections and baked goods. Vanillin is also used in the fragrance industry, in perfumes to mask unpleasant odors or tastes in medicines, livestock fodder, and cleaning products. Vanillin has been used as a chemical intermediate in the production of pharmaceuticals and other fine chemicals.

F. Use of the Enzyme Compositions of the Present Technology in Organic Synthesis In some embodiments, the composition of the present technology comprising laccase can be employed for several applications in organic synthesis for example, the oxidation of functional groups, the coupling of phenols and steroids.

In some embodiments, the composition of the present technology comprising laccase can be used to aerobically convert phenol to catechol. Catechol is the precursor to pesticides, flavors, and fragrances. Approximately 50% of synthetic catechol is consumed in the production of pesticides, the remainder being used as a precursor to fine chemicals such as perfumes and pharmaceuticals.

Catechol is a common building block in organic synthesis. Several industrially significant flavors and fragrances are prepared starting from catechol. Guaiacol is prepared by methylation of catechol and is then converted to vanillin. The related monoethyl ether of catechol, guethol, is converted to ethylvanillin, a component of chocolate confectioneries. 3-Trans-Isocamphylcyclohexanol, widely used as a replacement for sandalwood oil, is prepared from catechol via guaiacol and camphor. Piperonal, a flowery scent, is prepared from the methylene diether of catechol followed by condensation with glyoxal and decarboxylation.

The compositions of the present technology are useful to oxidize phenolic compounds (for example, phenols, polyphenols, meta substituted phenols), diamines and a variety of other components utilizing molecular oxygen. In some embodiments, the compositions of the present technology are useful in the synthesis of quinones by oxidizing phenols and catechols. A large scale industrial application of quinones is for the production of hydrogen peroxide. 2-Alkylanthraquinones are hydrogenated to the corresponding hydroquinones (quinizarins), which then transfer $H_2$ to oxygen.

Derivatives of quinones are common constituents of biologically relevant molecules (for example, Vitamin K1 is phylloquinone). Natural or synthetic quinones show a biological or pharmacological activity, and some of them show antitumoral activity and possess a number of biological properties, including some claims in herbal medicine. These applications include purgative (sennosides), antimicrobacterial (rhein- and saprorthoquinone), anti-tumor (emodin and juglone), inhibition of PGE2 biosynthesis (arnebinone and arnebifuranone) and anti-cardiovascular disease (tanshinone).

Many natural and artificial coloring substances (dyes and pigments) are quinone derivatives. They are second only to azo dyes in importance as dyestuffs, with particular emphasis on blue colors. Alizarin (2,3-dihydroxy-9,10-anthraquinone), extracted from the madder plant, was the first natural dye to be synthesized from coal tar.

G. Use of Enzyme Compositions in Food and Beverage Industry

In some embodiments, the compositions of the present technology comprising laccases can be applied to certain processes that enhance or modify the color appearance of food or beverage. The compositions of the present technology are useful in the elimination of undesirable phenolics, responsible for the browning, haze formation and turbidity development in clear fruit juice, beer and wine. In some embodiments, the compositions are used in different aspects of the food industry such as bioremediation, beverage processing, ascorbic acid determination, sugar beet pectin gelation, baking and as a biosensor.

VII. Kits

The compositions and methods provided herein can be used in various applications. For example, the compositions of the present technology can be provided in a kit, in some embodiments. The kit can comprise, for example, i) a laccase enzyme; ii) a plurality of nanoparticles comprising cuprous oxide, magnesium chloride, manganese chloride, or calcium chloride; and iii) instructions for combining the enzyme and the nanoparticles to form an enzyme composition. In some embodiments, the kit further includes instructions for applying the enzyme composition for the treatment of wide variety of organic and inorganic substrates. Additionally or alternatively, in some embodiments, the kit includes a composition comprising laccase enzyme in contact with nanoparticles comprising cuprous oxide, magnesium chloride, manganese chloride, or calcium chloride. In some embodiments, the kit further includes instructions for applying the enzyme composition for the treatment of wide variety of organic and inorganic substrates.

In some embodiments of the method, the enzyme comprises recombinant enzyme. In some embodiments, the enzyme is derived from a microorganism, such as a bacteria or fungus. For example, in some embodiments, the enzyme derived from one or more of *Pseudomonas marginalis, Azospirillum lipoferum, Streptomyces* sp., *Rhus vernicifera, Mycobacterium tuberculosis, Escherichia coli, Caulobacter crescentus, Pseudomonas syringae, Bordetella pertussis, Xanthomonas campestris, Pseudomonas aeruginosa, Mycobacterium avium, Pseudomonas putida, Rhodobacter capsulatus, Yersinia pestis, Campylobacter jejuni, Aquifex aeolicus, Physisporinus rivulosus, Melanocarpus albomyces, Agaricus blazei, Trametes versicolor, Pycnoporus sanguineus*, and/or *Basidiomycota* sp.

In some embodiments, the enzyme is purified from *Pseudomonas marginalis, Azospirillum lipoferum, Streptomyces* sp., *Rhus vernicifera, Mycobacterium tuberculosis, Escherichia coli, Caulobacter crescentus, Pseudomonas syringae, Bordetella pertussis, Xanthomonas campestris, Pseudomonas aeruginosa, Mycobacterium avium, Pseudomonas putida, Rhodobacter capsulatus, Yersinia pestis, Campylobacter jejuni, Aquifex aeolicus, Physisporinus rivulosus, Melanocarpus albomyces, Agaricus blazei, Trametes versicolor, Pycnoporus sanguineus*, and/or *Basidiomycota* sp. In some embodiments, the enzyme is recombinantly derived.

In some embodiments, the enzyme is recombinantly modified to further comprise a non-heterologous peptide tag. Exemplary non-heterologous peptide tags include but are not limited to $(His)_6$ tag, glutathione-S-transferase tag (GST), peptide fragments of human proto-oncoprotein MYC (for example, N-ILKKATAYIL-C(SEQ ID NO: 1), N-EQKLISEEDL-C(SEQ ID NO: 2)), peptide fragments of Influenza protein haemagglutinin (HA) for example, N-YPYDVP-C (SEQ ID NO: 3).

In some embodiments, the nanoparticle including a cuprous oxide, magnesium chloride, manganese chloride, or calcium chloride has a diameter of about 25 nm to about 500 nm. In some embodiments, the diameter is about 50 nm to about 400 nm. In some embodiments, the diameter is about 350 nm.

EXPERIMENTAL EXAMPLES

The present compositions and methods thus generally described, will be understood more readily by reference to the following examples, which are provided by way of illustration and are not intended to be limiting. The following is a description of the materials and experimental procedures used in the Examples.

Example 1

Purification of Laccase from *Pseudomonas marginalis* and *Escherichia coli* Laccase from *Pseudomonas marginalis*

In some embodiments, the laccase enzyme can be purified from *Pseudomonas marginalis*. This bacteria was isolated from termite soil. Bacterial laccase enzyme is purified by two consecutive processes. First ion exchange chromatography (CM Sepharose) can be used followed by gel filtration chromatography (Sephadex G-75).

Laccase from *Escherichia coli*

Laccase enzyme was purified from *Escherichia coli* ALK2 secreting laccase into the culture media. In one example, Laccase was purified from a 100-ml *E. coli* culture in Luria broth into which laccase was secreted. Cell-free supernatant was mixed with 10 ml CM-Sepharose pre-equilibrated with Tris-HCl buffer (25 mM, pH 8.5) and kept at 4° C. overnight. After leaving the mixture overnight, 10 ml of the mixture was loaded onto a column (10 ml bed volume). Bound compounds were eluted with Tris-HCl buffer (25 mM, pH 8) containing 0-1 M NaCl. Fractions of 1 ml were collected and those showing laccase activity were concentrated using a Macrosep 10 K unit and loaded onto a glass column packed with Sephadex G-75 (bed volume 30 ml) and equilibrated with the same Tris-HCl buffer. Elution of the proteins were performed using Tris-HCl buffer (25 mM, pH 8.5) and analyzed by 12% SDS polyacrylamide gel electrophoresis (PAGE). Protein markers and protein bands were stained by silver staining.

Example 2

Activity Assay of Laccase

The laccase activity was determined by syringaldzine assay which measured absorbance at 525 nm. Appropriate dilution of 1 ml supernatant was added to 3 ml of 25 mM Tris-HCl buffer, pH: 8.5, and then 2 ml substrate syringaldazine (solution in methanol and 1:2 dilution by Dioxan) was added to make a total assay system of 5 ml. The final concentration of syringaldzine was 1 mM, the concentration of $Cu^{2+}$ ion was 0.18 mM, concentration of laccase enzyme was 0.22 mg/ml, and concentration of the nanoparticle comprising cuprous oxide was 0.1 mM. The immediate color change from straw yellow to dark pink or violet was measured by spectrophotometer at 525 nm. The enzyme activities were measured at varying temperature, pH, and time in the presence or absence of nanoparticles comprising cuprous oxide.

Example 3

Preparation of a Composition Comprising Laccase Enzyme and Nanoparticles Comprising Cuprous Oxide Nanoparticles comprising cuprous oxide were purchased from Sigma-Aldrich (Catalog No. 678945). The composition comprising laccase enzyme was made by combining 0.22 mg/ml of the laccase enzyme with 0.1 mM of the nanoparticles comprising cuprous oxide in a reaction mixture comprising 25 mM Tris-HCl buffer, pH 9. The enzyme was incubated with the nanoparticle comprising cuprous oxide for 15 minutes at 50° C. For assays to determine thermal stability of the laccase enzyme treated with the nanoparticle comprising cuprous oxide, the enzyme was incubated with the nanoparticle from 30° C.-90° C. for 15-180 minutes.

The size and morphology of the particles was determined using transmission electron microscopy (TEM) (CM 200 CXPhilips at 160 kV). Nanoparticles comprising cuprous oxide had an average size of about 350 nm.

Example 4

Characterization of Laccase Enzyme with and without the Nanoparticles Comprising Cuprous Oxide A. Evaluation of the Kinetic Parameters The kinetic parameters of treated and untreated enzyme were evaluated to gain an insight into the tolerance of the purified laccase to temperature. For the enzyme kinetics experiments, the buffer (25 mM Tris-HCl, pH 8.5) was used without any supplementation of copper ions. In case of the laccase enzyme not treated with nanoparticles comprising cuprous oxide, the laccase enzyme is purified from bacterial culture media supplemented with 0.18 mM $CuSO_4$ to which it is secreted. In case of the composition comprising laccase enzyme and nanoparticles comprising cuprous oxide, the nanoparticles were added to each assay. Syringaldzine was used as the enzyme substrate. Varying concentration of syringaldzine (0.2 mM to 2 mM) was used to determine the kinetic parameters. The incubation was carried out at temperature of 50° C. or 80° C., 0.22 mg/ml of laccase enzyme in the presence or absence of 0.1 mM nanoparticles comprising cuprous oxide. The reaction was monitored spectrophotometrically at 525 nm.

The activation energy ($E_a$) was calculated for the temperature range of 40°-80° C. from the Arrhenius plot. The syringaldzine concentration used for this purpose was 1 mM.

The kinetic parameters, $K_m$, $V_{max}$ and the activation energy ($E_a$) of both treated and untreated purified laccase enzyme were calculated according to the methods of Liao, et al., (1997) J. Appl. Microbiol. 83, 10-16. The results of the study are shown in the Table 1 below.

TABLE 1

Km, Vmax and activation energy (Ea): Nanoparticle comprising cuprous oxide ($Cu_2O$ NP) treatment enhances the enzyme substrate specificity and lowers the activation energy as compared to untreated enzyme.

| Enzyme | $K_m$ at 50° C. (mM) | Vmax at 50° C. (Unit/ml) | Km at 80° C. (mM) | Vmax at 80° C. (Unit/ml) | Ea (KJ/mol) |
|---|---|---|---|---|---|
| Laccase treated with $Cu_2O$ NP | 3.33 | 210 | 2 | 157 | −8.069 |
| Laccase untreated | 4 | 150 | 5.63 | 127 | 38.12 |

The laccase enzyme treated with nanoparticle comprising cuprous oxide ($Cu_2O$ NP) is more active than the untreated laccase enzyme. The treated enzyme has higher $V_{max}$ at both 50° C. and 80° C. Additionally, the affinity for the substrate is greater for the treated laccase enzyme than the untreated enzyme at 80° C. The $K_m$ of the treated enzyme is nearly half of the untreated enzyme. Additionally, the activation energy of the treated enzyme is much lower than the untreated enzyme.

Thus, treating the laccase enzyme with nanoparticles comprising cuprous oxide increases the enzyme activity and lowers activation energy. Additionally, treating the laccase enzyme with nanoparticles comprising cuprous oxide increases the affinity towards the substrate at higher temperatures, such as at 80° C.

B. Thermotolerance and Inactivation Kinetics of Treated and Untreated

The thermal inactivation of treated and untreated purified laccase was examined with respect to kinetics. 0.22 mg/ml of the laccase enzyme purified from E. coli was treated with 0.1 mM concentration of nanoparticles comprising cuprous oxide. The reaction mixture included 25 mM Tris-HCl, pH 8.5 and 1 mM of syringaldzine. After adding substrate, immediate color change from straw yellow to purple confirmed the laccase activity. The reaction was monitored at 525 nm. To observe the thermal stability, cuprous oxide nanoparticle ($Cu_2O$ NP) and $Cu_2O$ NP untreated purified laccase samples were subjected to temperatures between 40 and 80° C. (313-353 K) for up to 10 minutes. Inactivation parameters comprising half-life ($t_{1/2}$), decay rate constant (k) and deactivation energy (Ed) were calculated according to Ortega et al., (2004) Int. J. Food Sci. Technol. 39, 631-639.

Figure 2A:
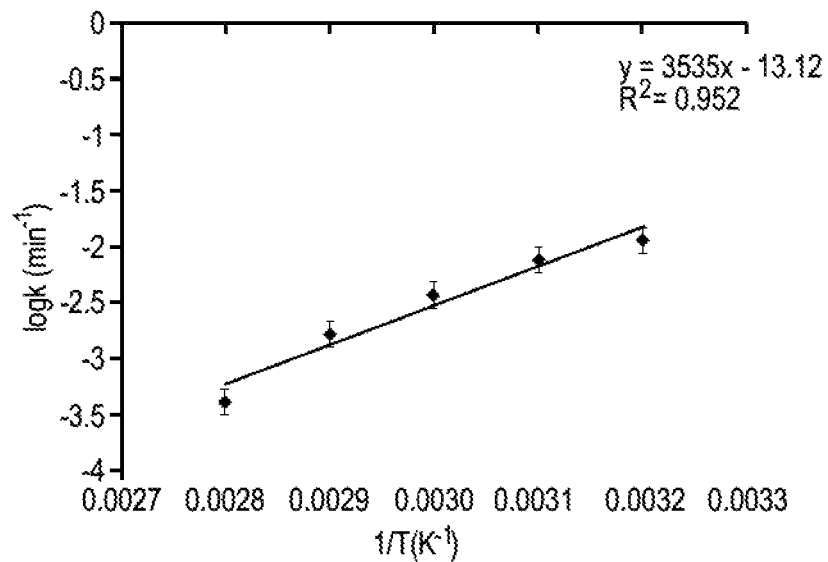
FIGS. 2(a)-(b) show an Arrhenius plot for heat activation for nanoparticle comprising cuprous oxide untreated (FIG. 2(a)) and treated (FIG. 2(b)) laccase.
Figure 2B:
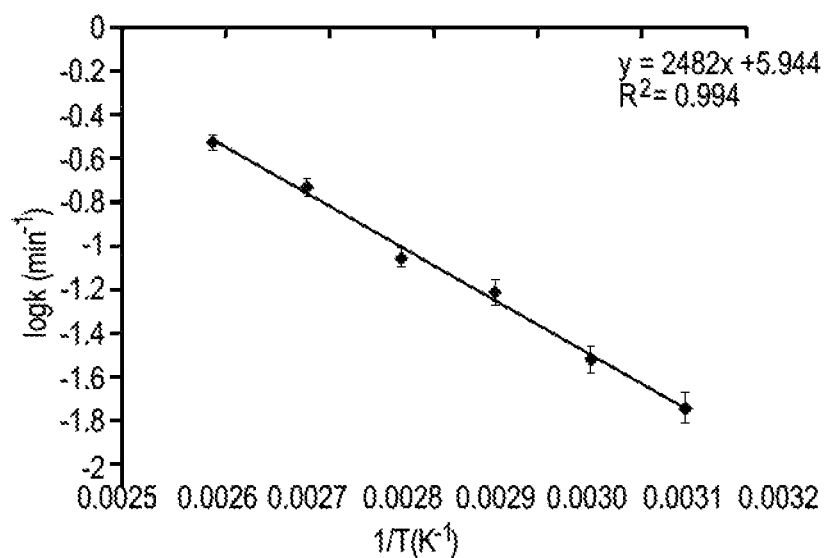

After the pre-incubation, the enzyme activity was determined by the syringaldazine assay as described previously. A semi-logarithmic plots of residual activity versus time (between 40-80° C.) for both cases were linear. The plots suggested that $Cu_2O$ NP untreated laccase was heat inactivated with first order kinetics, but the $Cu_2O$ NP treated enzyme was heat activated with first order kinetics. The half-life ($t_{1/2}$) values and the deactivation energy ($E_d$) according to the plots (FIG. 2; FIG. 2(a) untreated, FIG. 2(b) treated enzyme) and shown in Tables 2 and 3 below.

TABLE 2

Variation of kinetic parameters for untreated laccase within 40-80° C.

| Pre-Incubation Temperature(K) | Decay Constant [k] (min$^{-1}$) | Half Life [$t_{1/2}$] (min) | $E_d$ (kJ/mol) |
|---|---|---|---|
| 313 | 0.0021 | 330 | |
| 323 | 0.0179 | 38.72 | |
| 333 | 0.0297 | 23.33 | −47.532 |
| 343 | 0.061 | 11.36 | |
| 353 | 0.881 | 7.86 | |

TABLE 3

Variation of kinetic parameters for treated laccase within 40-80° C.

| Pre-Incubation Temperature(K) | Decay Constant[k] (min$^{-1}$) | Half Life [$t_{1/2}$] (min) | $E_d$ (kJ/mol) |
|---|---|---|---|
| 313 | 0.0115 | 60 | |
| 323 | 0.0078 | 88.85 | |
| 333 | 0.0038 | 182.27 | 36.132 ± 0.325 |
| 343 | 0.0033 | 210 | |
| 353 | 0.0021 | 330 | |

Based on the results in Tables 2 and 3, it is shown that the addition of nanoparticle comprising cuprous oxide increases the half-life of laccase enzyme and also increases the deactivation energy ($E_d$) compared to untreated enzyme at a temperature of 80° C.

C. Optimum Temperature and pH of Treated and Untreated Laccase Enzyme with Nanoparticles Comprising Cuprous Oxide To measure the optimum temperature of both the treated and untreated laccase enzyme, in one testing condition, the treated and untreated enzyme was held at different temperatures ranging from 30° C. to 100° C. (for treated enzyme) and 20° C. to 100° C. (for the untreated enzyme) for 10 minutes. After 10 minutes, enzyme activity was determined by the syringaldazine assay, as previously described. The reaction was monitored at 525 nm. The activity of the enzyme relative to the highest activity, which was given a value of 100 (relative activity of the enzyme) was plotted against different temperatures and is shown in FIG. 3(a) treated, and FIG. 3(b) untreated enzyme.

The laccase enzyme treated with nanoparticles comprising cuprous oxide retained at least 50% of the relative activity over a wider range of temperatures 30° C.-90° C. as compared to the untreated enzyme. The untreated enzyme retained at least 50% of its activity over a narrow range of temperatures of 20°-70° C. Additionally, the treated enzyme showed the highest activity at 80° C. while the untreated enzyme showed the highest activity at 50° C. Thus, the treated enzyme worked better at a higher temperature compared to the untreated enzyme.

To determine an optimal pH, a sample of the treated and untreated enzyme was placed in a buffer having pH ranging from 3-12. The reaction mixture was not supplemented with external copper ion. Enzyme activity was determined to measure optimum pH by the syringaldazine assay, as previously described. The reaction was monitored at 525 nm.

Figure 4A:
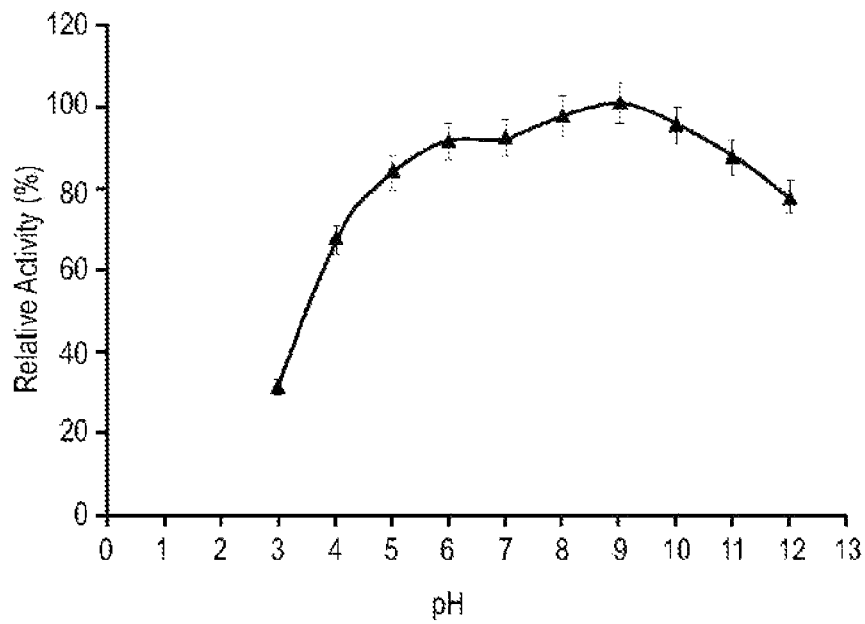
FIGS. 4(a)-(b) illustrate the pH dependence of laccase enzyme treated (FIG. 4a) and untreated (FIG. 4b) with nanoparticles comprising cuprous oxide.
Figure 4B:
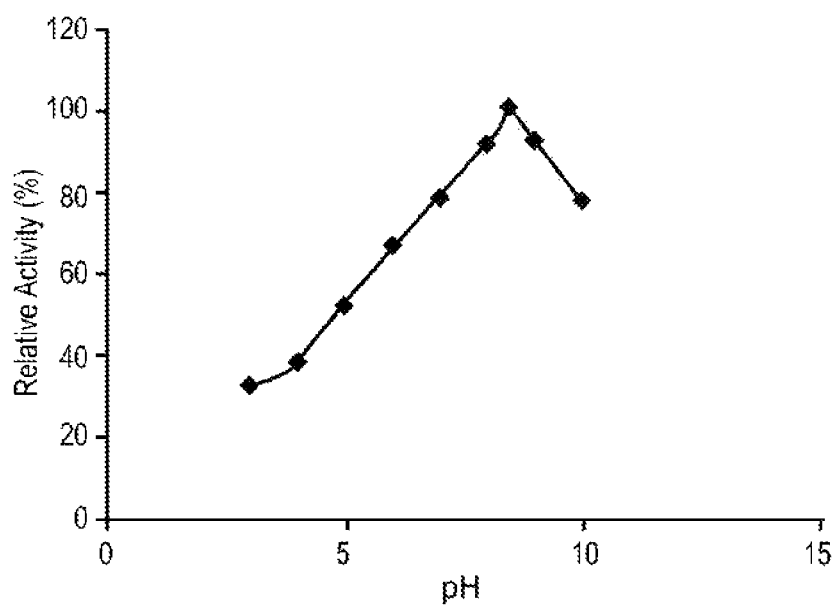

The activity of the enzyme relative to the highest activity, which was given a value of 100 (relative activity of the enzyme) was plotted against different temperatures and is shown in FIG. 4(a) treated, and 4(b) untreated enzyme.

The laccase enzyme treated with nanoparticles comprising cuprous oxide retained at least 50% of the relative activity over a wider range of pH 4-12 as compared to the pH range of 7-10 for the untreated enzyme.

Example 5

Comparison of Laccase Enzyme Activity with and without the Nanoparticles Comprising Cuprous Oxide A. Enhancement of Laccase Activity by Nanoparticles Comprising Cuprous Oxide Purified laccase enzyme was incubated with syringaldazine substrate and varying concentrations of cuprous oxide nanoparticle in a reaction mixture without supplementation with external copper ion. The reaction was monitored at 525 nm. The laccase enzyme treated with nanoparticle comprising cuprous oxide in the absence of cuprous ion in buffer showed significantly higher activity than only cuprous ion supplemented enzyme without nanoparticle. Moreover, laccase enzyme treated with nanoparticle comprising cuprous oxide showed higher activity than laccase enzyme treated with both cuprous ion (in buffer) and nanoparticle.

B. Nanoparticle Supplementation Promotes Retention of Laccase Activity

Figure 5A:
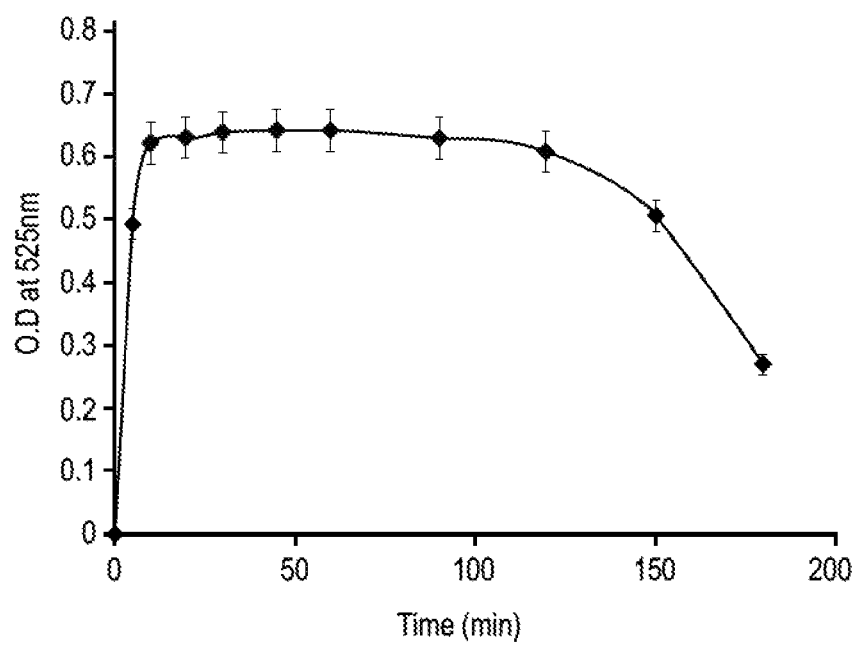
FIGS. 5(a)-(b) illustrate the results of a comparative study of a laccase activity assay with (FIG. 5(a)) and without (FIG. 5(b)) nanoparticles comprising cuprous oxide over increasing time at 80° C.
Figure 5B:
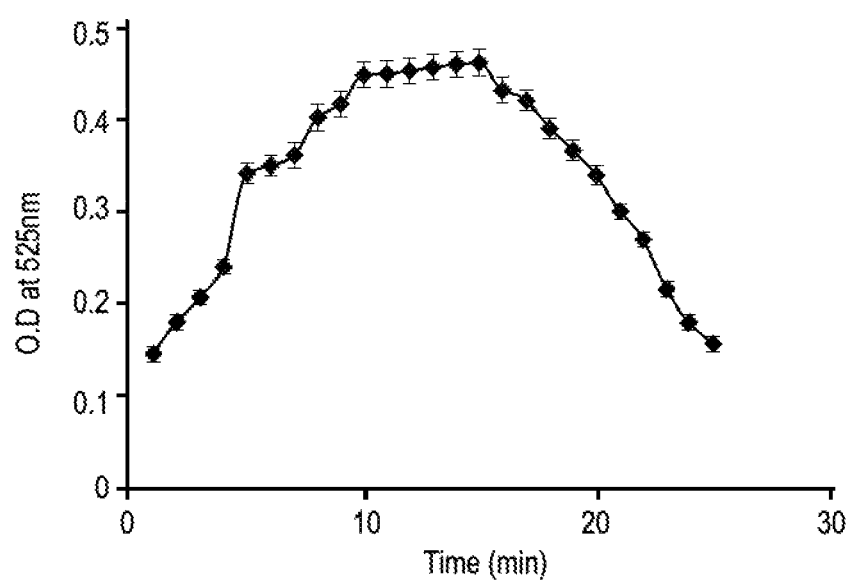
Figure 6A:
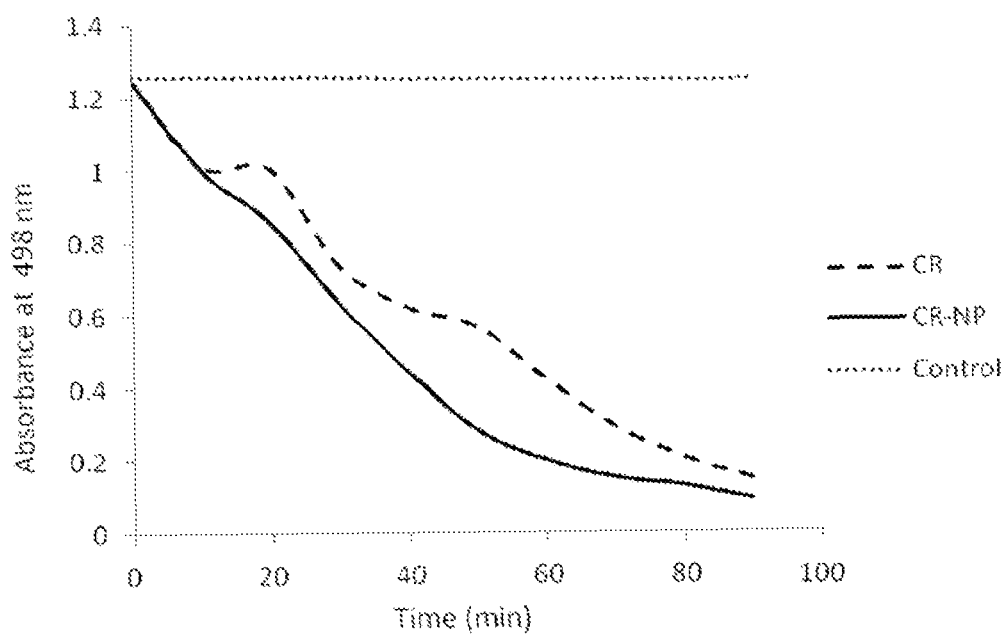
FIGS. 6(a)-(e) illustrate the results of a comparative study of dye decolorization with laccase enzyme; (a) CR-Congo red, (b) CB-Cotton blue, (c) BB-Bromophenol blue, (d) MG-Malachite green and (e) MO-Methyl orange with nanoparticles treated and untreated laccase enzyme. For each of FIGS. 6(a)-(e), the dotted line represents the no enzyme control; the dashed line represents enzyme without nanoparticle treatment; the solid line represents enzyme treated with nanoparticles comprising cuprous oxide.
Figure 6B:
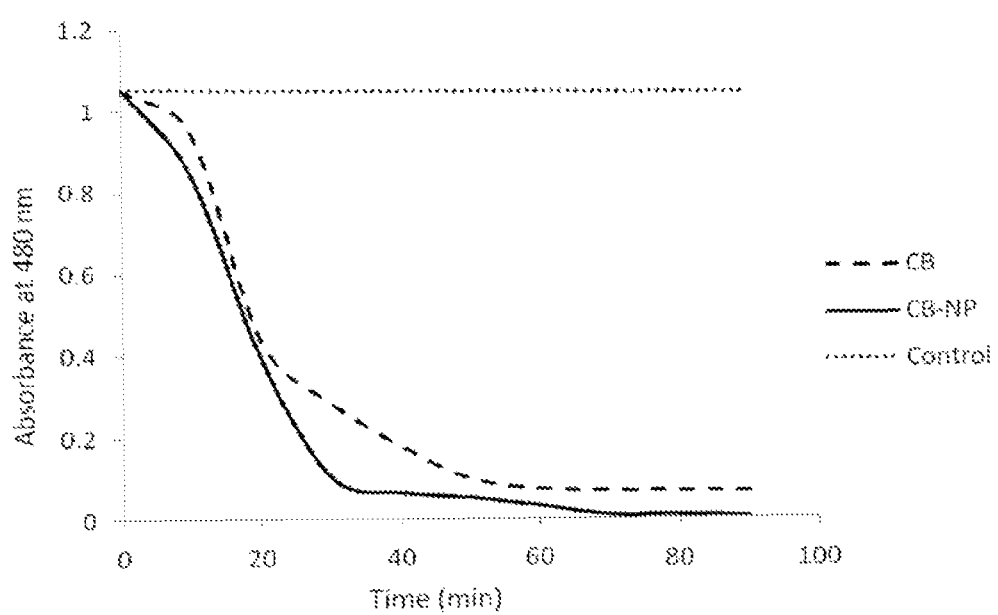
Figure 6C:
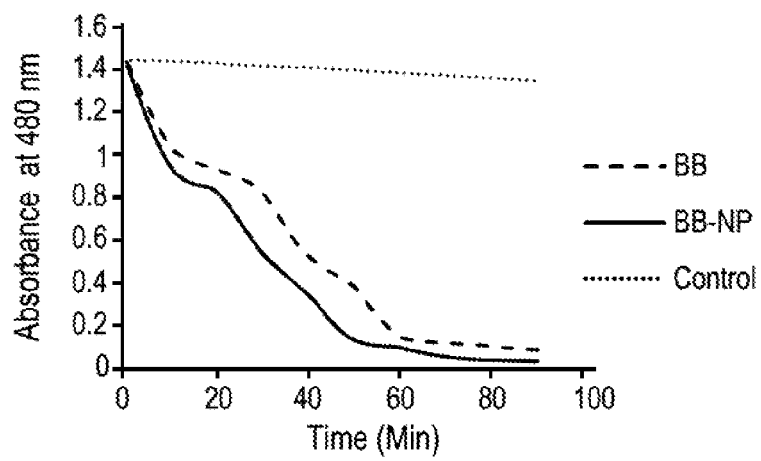
Figure 6D:
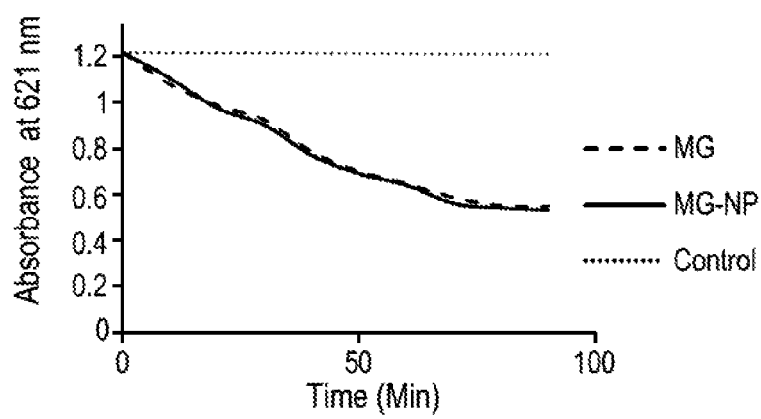
Figure 6E:
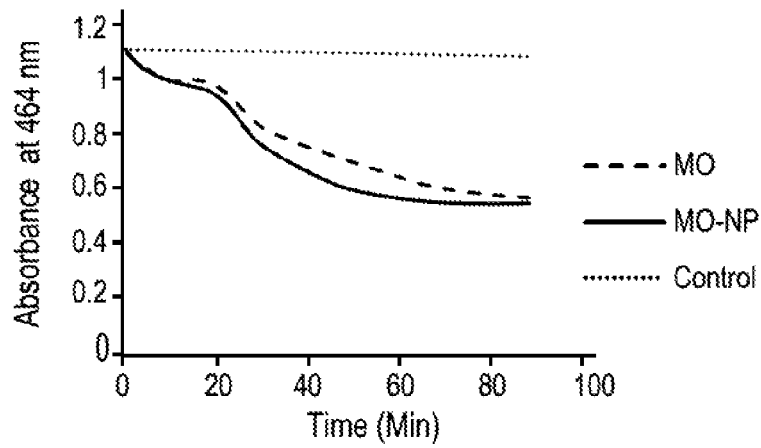
Figure 7A:
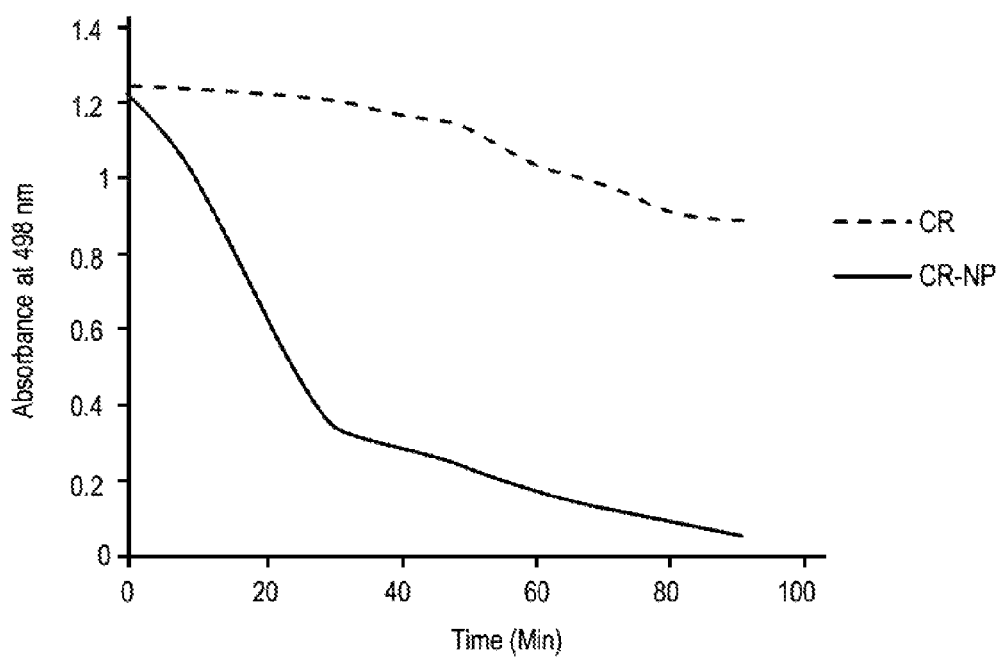
FIGS. 7(a)-(d) illustrate the results of a time kinetic study for dye decolorization using laccase enzyme in the presence of nanoparticles comprising cuprous oxide; (a) CR-Congo red, (b) CB-Cotton blue, (c) BB-Bromophenol blue and (d) MG-Malachite green.
Figure 7B:
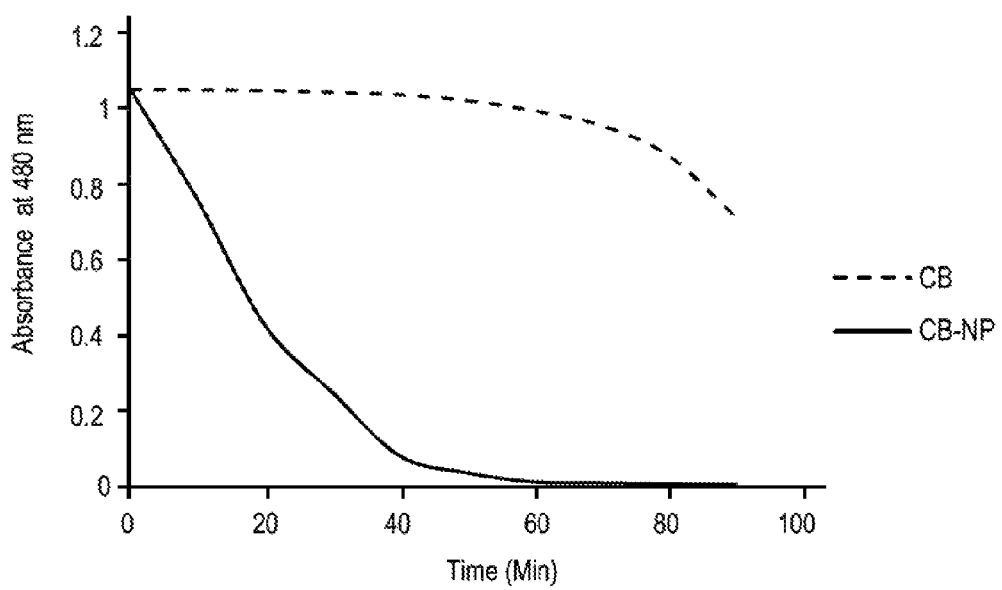
Figure 7C:
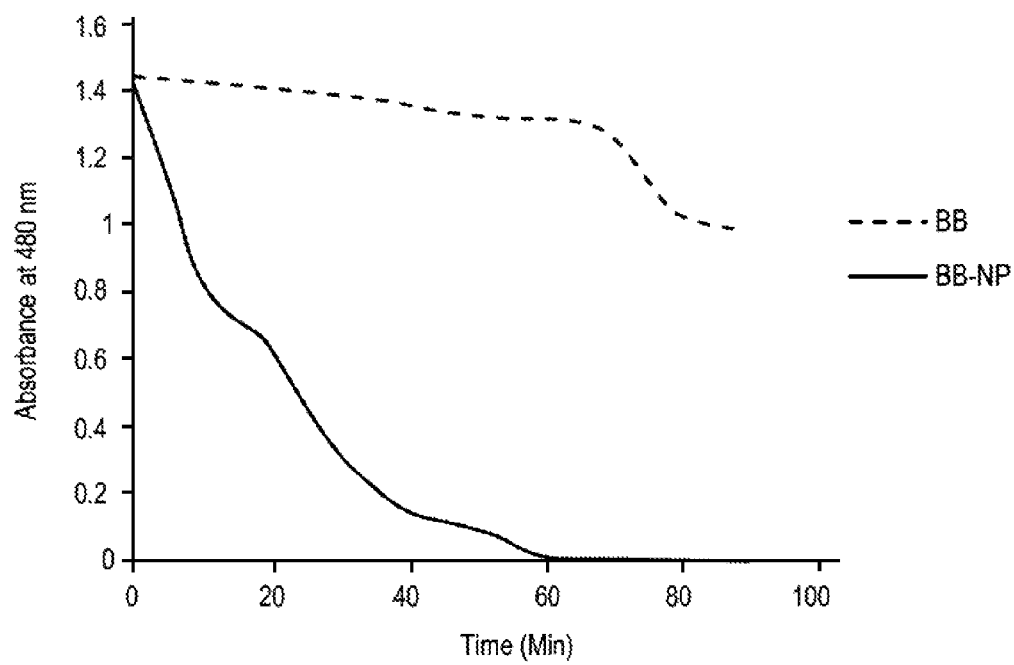
Figure 7D:
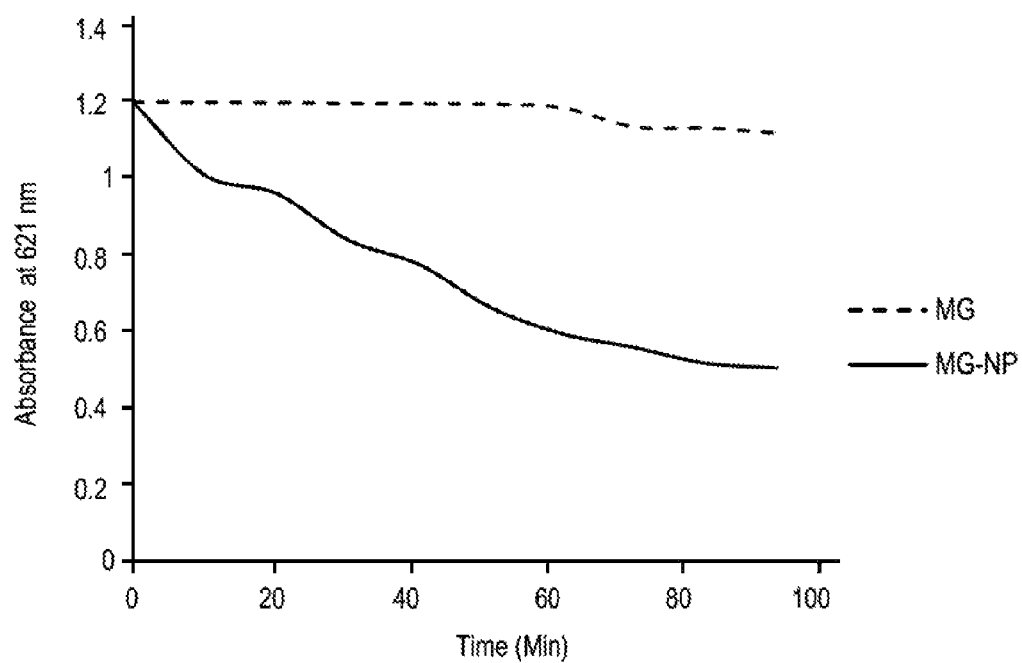

The alteration (if any) in enzyme activity with time, in the presence or absence of nanoparticles, was examined via time kinetics. Laccase activities were measured by the syringaldazine method for a total duration of two hours after incubation with substrate at 50° C. The reaction mixture included 0.22 mg/ml of the laccase enzyme, 1 mM of syringaldazine, with or without 0.1 mM nanoparticles comprising cuprous oxide. It was observed that enzyme without nanoparticle treatment showed optimum activity at 15 minutes, after which the activity decreased with time. However, nanoparticle treated enzyme retained activity for longer period of time (FIG. 5(a) treated, 5(b) untreated).

Figure 3:
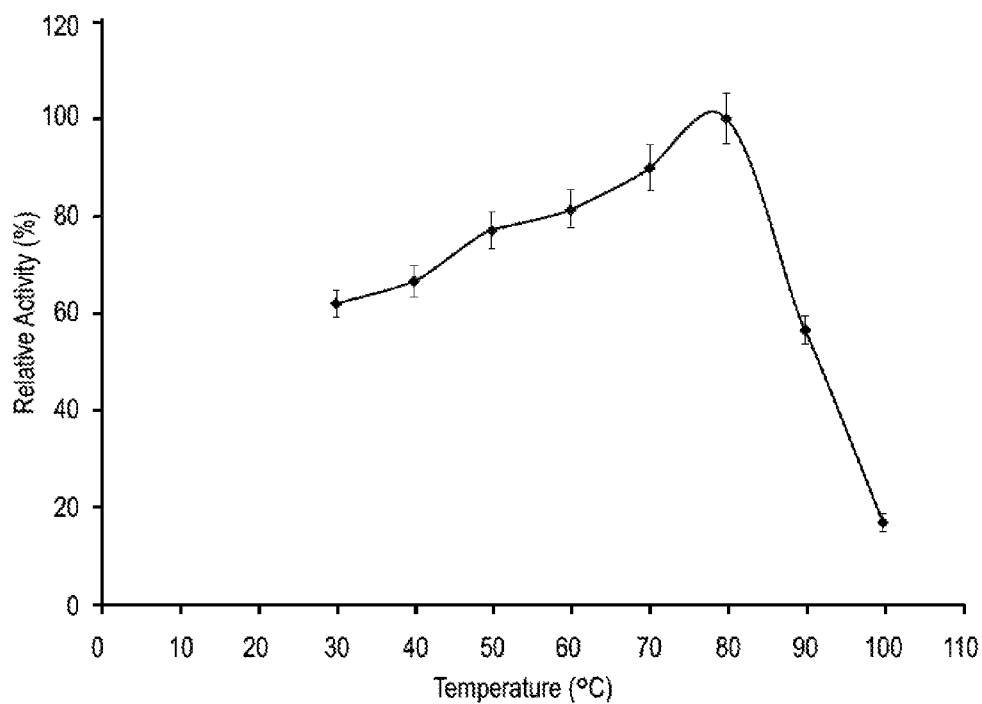
FIGS. 3(a)-(b) illustrate the results of a comparative study of a laccase activity assay of laccase enzyme treated (FIG. 3(a)) and untreated (FIG. 3(b)) with nanoparticles comprising cuprous oxide over increasing temperature 30° C.-100° C.
Figure 3:
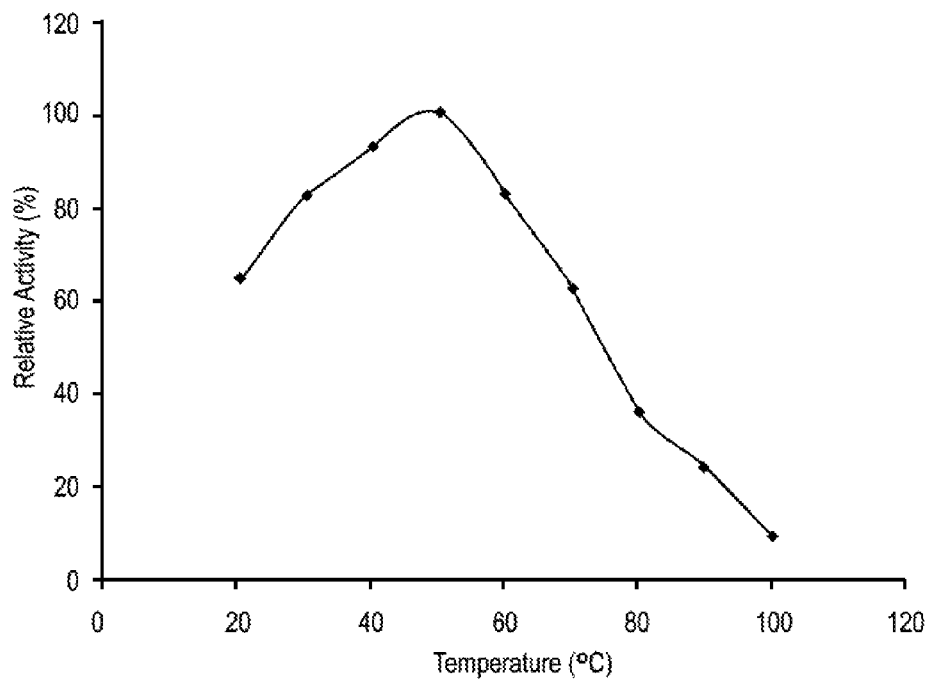

C. Nanoparticle Supplementation Improves Temperature Tolerance of Laccase Enzyme and Enhances its Activity The temperature dependence of laccase activity was assessed in the presence and absence of nanoparticle comprising cuprous oxide. Samples were incubated for three hours at various temperatures before measuring the enzyme activity. It was found that at 80° C. the nanoparticle treated enzyme demonstrated approximately three times the activity of untreated enzyme (FIG. 3). Moreover, the treated enzyme incubated at 80° C. for two hours showed much more activity than both treated and untreated enzymes incubated at 50° C. for 2 hours (FIG. 3). The reaction mixture included 0.22 mg/ml of the laccase enzyme, 1 mM of syringaldazine, with or without 0.1 mM nanoparticles comprising cuprous oxide.

D. Nanoparticle Decolorization of Dye is Improved with Treated Laccase Enzyme

Phenolic (bromophenol blue) and azo dyes (congo red, cotton blue, malachite green, methyl orange) were treated with 1 ml of 0.22 mg/ml of purified laccase enzyme treated or untreated with nanoparticle comprising cuprous oxide ($Cu_2O$ NP). In case of the laccase enzyme not treated with nanoparticles comprising cuprous oxide, the laccase enzyme is purified from bacterial culture media supplemented with 0.18 mM $CuSO_4$ to which it is secreted. In case of the laccase enzyme treated with nanoparticles comprising cuprous oxide, 0.22 mg/ml of the enzyme was treated with 0.1 mM of nanoparticles comprising cuprous oxide for 90 minutes at 50° C. These dyes were incubated with laccase at 50° C. and 80° C. for 90 minutes in the presence and absence of nanoparticle comprising cuprous oxide. At 10 minutes intervals the corresponding absorbance were taken for each sample to monitor the decolorization. For cotton blue, bromophenol blue and congo red, the decolorization effect was very prominent after 90 minutes. There was a decrease of absorbance with increasing time at 50° C. (FIGS. 6(a)-(e); dotted line represents no enzyme control; dashed line indicates untreated enzyme and solid line indicates treated enzyme). FIG. 7 shows the activity of treated and untreated enzyme an 80° C. At 80° C. in the absence of $Cu_2O$ NP, untreated laccase is unable to decolorize these dyes; however, in presence of $Cu_2O$ NP, at 80° C. laccase decolorized these dyes faster than $Cu_2O$ NP treated laccase at 50° C. (FIGS. 7(a)-(d); dashed line represents untreated enzyme; solid line represents treated enzyme). In the presence of $Cu_2O$ NP, laccase can act faster than the untreated enzyme at both 50° C. and 80° C. The reaction mixture included 0.22 mg/ml of the laccase enzyme, 1 mM of syringaldazine, with or without 0.1 mM nanoparticles comprising cuprous oxide.

Figure 8:
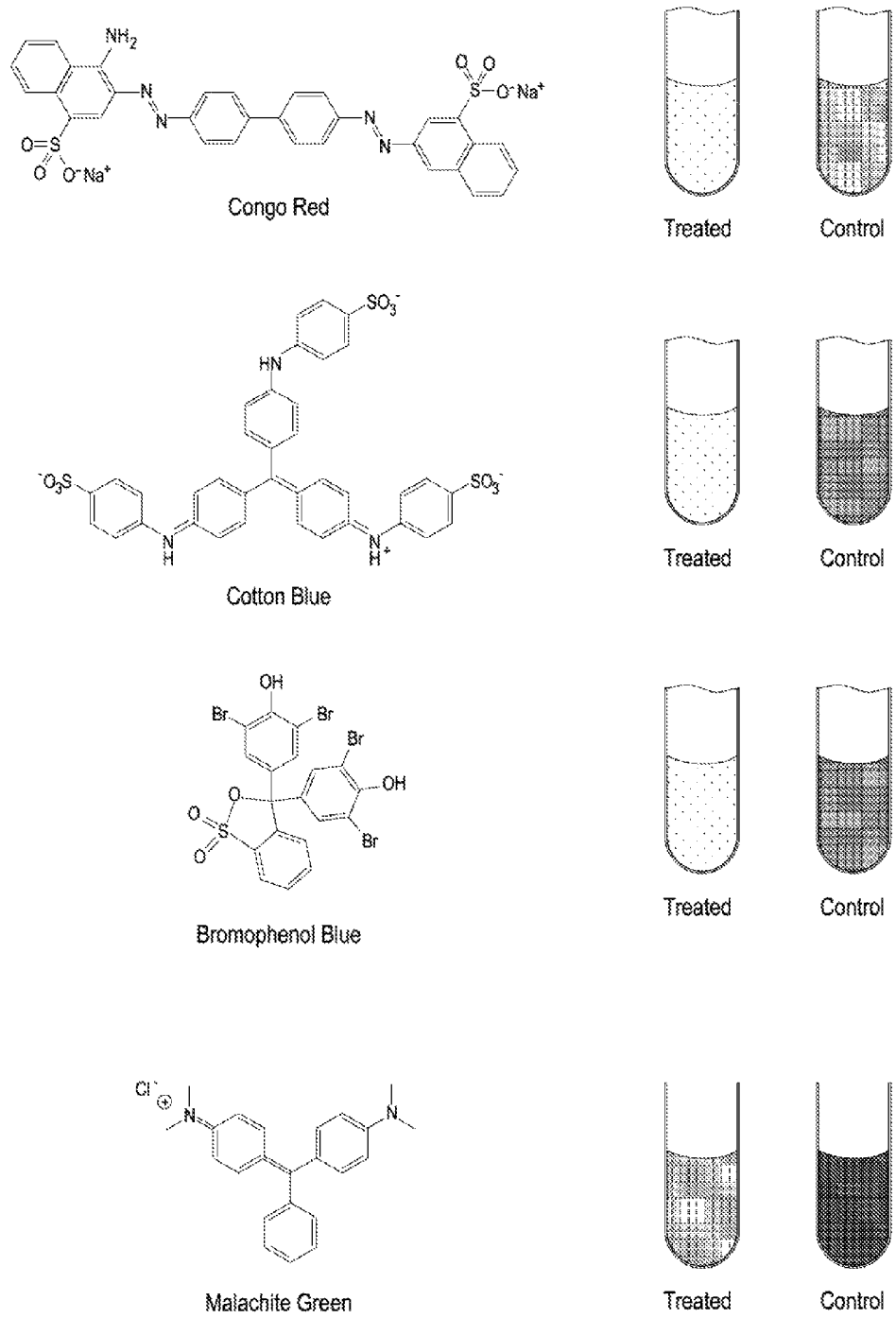
FIG. 8 illustrates dye decolorization by purified bacterial laccase treated with nanoparticles comprising cuprous oxide.

FIG. 8 shows the activity of nanoparticle-treated enzyme on dye in solution. The changes in color for bromophenol blue and congo red were very prominent after 90 minutes (FIG. 8).

E. Nanoparticle Supplementation Improves Detergent Tolerance of Laccase Enzyme

The effect of detergent Triton-X100 (obtained from Sigma Chemical Co., St. Louis, Mo.) on Laccase enzyme activity was assessed in the presence and absence of nanoparticles. A series of samples were prepared, each including 0.22 mg/ml of the laccase enzyme, 1 mM of syringaldazine, and 0.1 mM nanoparticles that included cuprous oxide. Different concentrations of the detergent (0 wt %, 0.5 wt %, 1.0 wt %, 1.5 wt % and 2.0 wt %) were added to each of the samples, and the samples were incubated at 50° C. for 1 hour. The same samples were also prepared but without the nanoparticles.

Figure 11:
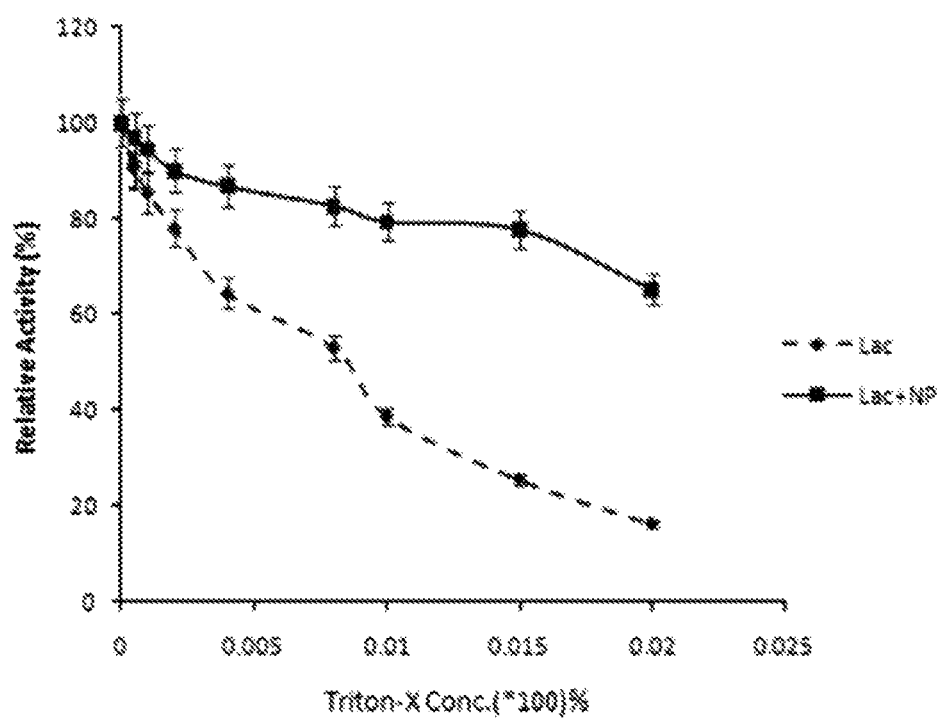
FIG. 11 illustrates the relative activities of laccase enzyme treated and untreated with nanoparticles comprising cuprous oxide, in the presence of increasing concentrations of a detergent.

FIG. 11 shows the activity of the nanoparticle treated laccase enzyme (represented by graph with square shaped symbol) and the untreated Laccase enzyme (represented by graph with diamond shaped symbol) against increasing concentrations of the detergent. It was observed that at 1.5 wt % concentration of the detergent, the fall in relative activity of the untreated enzyme was 74.8%, while the relative decrease in activity of the nanoparticle treated enzyme was only 22.2%. Hence, the nanoparticle treated Laccase enzyme retained its activity in the presence of the detergent better than the untreated enzyme, making it substantially detergent tolerant.

Example 6

Enhancement of Laccase Activity in Presence of Copper Sulfate, Magnesium Chloride, Manganese Chloride, Calcium Chloride, and Cobalt Chloride Copper sulfate, magnesium chloride, manganese chloride, calcium chloride, cobalt chloride, ferric chloride, sodium fluoride, or sodium cyanide were added to a buffer comprising 1 mM syringaldazine substrate; 25 mM Tris-HCl, pH 8.5 to a final concentration of 1 mM. The immediate color change from straw yellow to dark pink or violet was measured by spectrophotometer at 525 nm.

Figure 10:
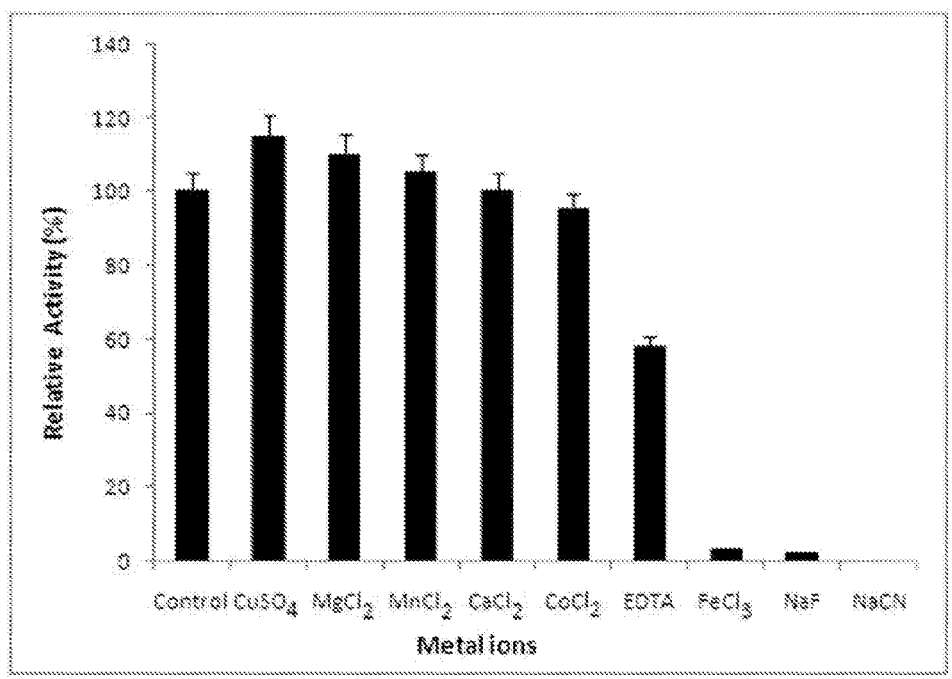
FIG. 10 illustrates relative activities of laccase enzyme in the presence of cupric sulfate, magnesium chloride, manganese chloride, calcium chloride, cobalt chloride, ferric chloride, sodium fluoride and sodium cyanide.

The relative laccase activity with respect to a control was measured in the presence of various salts and plotted. The enzyme activity was stimulated by the divalent cations $Cu^{2+}$, $Mn^{2+}$ and $Mg^{2+}$. The control reaction comprised 1 mM syringaldazine substrate; 25 mM Tris-HCl, pH 8.5, 0.22 mg/ml of purified laccase enzyme. The activity of laccase was increased up to 20%, 15% and 10% in presence of copper, magnesium and manganese ions, respectively. Calcium ion also slightly activated the enzyme activity by 5%. Inhibition of enzyme activity was observed in presence of EDTA (42%). In the presence of $Fe^{3+}$, NaF and NaCN, enzyme activity was reduced by 97%, 98% and 100% respectively (FIG. 10).

Example 7

Comparison of Laccase Enzyme Activity with and without the Nanoparticles Comprising Magnesium Chloride, Manganese Chloride, Calcium Chloride, and Cobalt Chloride Enhancement of Laccase Activity Purified laccase enzyme is incubated with syringaldazine substrate and varying concentrations of nanoparticle comprising magnesium chloride, manganese chloride, or calcium chloride in a reaction mixture without supplementation with external magnesium chloride, manganese chloride, calcium chloride, or cobalt chloride. The reaction is monitored at 525 nm. The laccase enzyme is treated with nanoparticle comprising magnesium chloride, manganese chloride, or calcium chloride in the absence of magnesium, manganese, or calcium ions in buffer shows significantly higher activity than only magnesium, manganese, or calcium ion supplemented enzyme without nanoparticles.

Temperature Tolerance

At 80° C., the activity of laccase enzyme with nanoparticle comprising magnesium chloride, manganese chloride, or calcium chloride is significantly higher than the activity of untreated enzyme.

pH Dependency

Additionally, the laccase enzyme with nanoparticle comprising magnesium chloride, manganese chloride, or calcium chloride retains its activity over a wider range of pH 4-12 as compared to the pH range of 7-10 for the untreated enzyme.

Example 8

Application of Laccase Enzyme Activity with Nanoparticles Comprising Cuprous Oxide for Bio-Bleaching of Ramie Fiber A piece of ramie fibre of 10 grams was incubated in 500 ml of laccase secreting *E. coli* culture medium for 24 hours in presence or absence of nanoparticles comprising cuprous oxide and examined for the degree of bleaching/decolorization at room temperature.

Figure 9:
FIGS. 9(a)-(b) show bio-bleaching of ramie fiber by laccase enzyme untreated (a) and treated (b) with nanoparticle comprising cuprous oxide.

The ramie fiber was bleached more extensively by the laccase enzyme in presence of nanoparticles comprising cuprous oxide than in absence of the nanoparticles. (FIG. 9).

EQUIVALENTS

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed:

1. A composition comprising:
   at least one nanoparticle comprising cuprous oxide; and
   at least one purified laccase enzyme in contact with the nanoparticle comprising cuprous oxide, wherein the enzyme is not immobilized on the nanoparticle.

2. The composition of claim 1, wherein the nanoparticle has a diameter of about 50 nm to about 200 nm.

3. The composition of claim 1, wherein the enzyme is a *Pseudomonas marginalis*, *Azospirillum lipoferum*, *Streptomyces* sp., *Rhus vernicifera*, *Mycobacterium tuberculosis*, *Escherichia coli*, *Caulobacter crescentus*, *Pseudomonas syringae*, *Bordetella pertussis*, *Xanthomonas campestris*, *Pseudomonas aeruginosa*, *Mycobacterium avium*, *Pseudomonas putida*, *Rhodobacter capsulatus*, *Yersinia pestis*, *Campylobacter jejuni*, *Aquifex aeolicus*, *Physisporinus rivulosus*, *Melanocarpus albomyces*, *Agaricus blazei*, *Trametes versicolor*, *Pycnoporus sanguineus*, or *Basidiomycota* sp. enzyme.

4. The composition of claim 1, wherein the enzyme in the composition has one or more of the following characteristics:
   an increased activity as compared to the same enzyme that is not in contact with the nanoparticle comprising cuprous oxide;
   an increased activity towards syrilgaldazine;
   is more thermostable as compared to the same enzyme that is not in contact with the nanoparticle comprising cuprous oxide.

5. The composition of claim 1, wherein the enzyme in the composition has one or more of the following characteristics:
   an increased activity at a temperature of about 70° C. to about 100° C. as compared to the same enzyme that is not in contact with the nanoparticle comprising cuprous oxide;
   an increased activity at a temperature of about 70° C. to about 100° C. and is more thermostable as compared to the same enzyme that is not in contact with the nanoparticle comprising cuprous oxide;
   a longer half-life as compared to the same enzyme that is not in contact with the nanoparticle comprising cuprous oxide;
   a decreased pH dependency as compared to the same enzyme that is not in contact with the nanoparticle comprising cuprous oxide;
   is more detergent tolerant as compared to the same enzyme that is not in contact with the nanoparticle comprising cuprous oxide.

6. The composition of claim 1, wherein the enzyme comprises a recombinant enzyme.

7. The composition of claim 6, wherein the recombinant enzyme comprises a peptide tag.

8. The composition of claim 7, wherein the peptide tag is selected from the group consisting of a $(His)_6$ tag, a glutathione-S-transferase tag (GST), a MYC tag, and an influenza protein haemagglutinin (HA) tag.

9. The composition of claim 1, wherein the laccase is purified from *Pseudomonas marginalis*.

10. The composition of claim 1, wherein the laccase is purified from *Escherichia coli*.

11. A method of making a stabilized enzyme composition, the method comprising:
  combining:
    at least one nanoparticle comprising cuprous oxide; and
    a purified laccase enzyme;
    to form a mixture, wherein the enzyme is in contact with the nanoparticle comprising cuprous oxide, and wherein the enzyme is not immobilized on the nanoparticle.

12. The method of claim 11, wherein combining the enzyme and at least one nanoparticle comprising cuprous oxide is carried out at 50° C.

13. The method of claim 11, wherein combining the enzyme and at least one nanoparticle comprising cuprous oxide is carried out at 80° C.

14. The method of claim 11, wherein combining the enzyme and at least one nanoparticle comprising cuprous oxide is carried out at pH between 3-12.

15. A method of treating a substrate, the method comprising:
  contacting the substrate with a composition comprising:
    at least one of nanoparticles comprising cuprous oxide; and
    a purified laccase enzyme;
    under conditions in which the enzyme is in contact with the nanoparticle comprising cuprous oxide, and the substrate, wherein the enzyme is not immobilized on the nanoparticle.

16. The method of claim 15, wherein the contacting is carried out at a temperature of about 30° C. to about 80° C.

17. The method of claim 15, wherein the contacting is carried out at a pH of about 3 to about 12.

18. The method of claim 15, wherein the contacting is carried out at a pH of about 9.

19. The method of claim 15, wherein the contacting is carried out from about 10 minutes to about 120 minutes.

20. The method of claim 15, wherein the substrate comprises a phenolic hydroxyl group.

21. The method of claim 15, wherein the substrate comprises a textile, wool, biocomposite, wastewater, paper, wood pulp, soil, animal feed, food, beverage, herbicide, pesticide, dye, pigment or combinations thereof.

22. The method of claim 15, wherein the substrate comprises wood pulp comprising lignin.

23. The method of claim 15, wherein contacting the substrate with the composition results in color reduction or decolorization of the substrate.

24. The method of claim 15, wherein contacting the substrate with the composition results in reduction or removal of browning or haze from the substrate.

* * * * *

UNITED STATES PATENT AND TRADEMARK OFFICE
CERTIFICATE OF CORRECTION

PATENT NO. : 9,493,763 B2  
APPLICATION NO. : 14/413635  
DATED : November 15, 2016  
INVENTOR(S) : Mukhopadhyay et al.

Page 1 of 1

It is certified that error appears in the above-identified patent and that said Letters Patent is hereby corrected as shown below:

In the Specification

In Column 1, Line 9, delete "§371" and insert -- § 371 --, therefor.

In Column 12, Line 59, delete "90 C.," and insert -- 90° C., --, therefor.

In Column 13, Line 28, delete "90 C.," and insert -- 90° C., --, therefor.

In Column 22, Line 29, delete "Km, Vmax and activation energy (Ea):" and insert -- $K_m$, $V_{max}$ and activation energy ($E_a$): --, therefor.

In Column 22, in Table 1, delete

| Enzyme | $K_m$ at 50° C. (mM) | Vmax at 50° C. (Unit/ml) | Km at 80° C. (mM) | Vmax at 80° C. (Unit/ml) | Ea (KJ/mol) |

" and insert

| Enzyme | $K_m$ at 50° C. (mM) | $V_{max}$ at 50° C. (Unit/ml) | $K_m$ at 80° C. (mM) | $V_{max}$ at 80° C. (Unit/ml) | $E_a$ (KJ/mol) |

--, therefor.

Signed and Sealed this  
Twenty-eighth Day of March, 2017

Michelle K. Lee  
*Director of the United States Patent and Trademark Office*